United States Patent
Patterson et al.

(10) Patent No.: US 10,555,891 B2
(45) Date of Patent: Feb. 11, 2020

(54) METHODS FOR TREATING CHEMICALLY TREATED HAIR

(71) Applicant: L'OREAL, Paris (FR)

(72) Inventors: Kwana Patterson, Clark, NJ (US); Barbara Mitchell, Clark, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 141 days.

(21) Appl. No.: 15/604,060

(22) Filed: May 24, 2017

(65) Prior Publication Data
US 2018/0338900 A1  Nov. 29, 2018

(51) Int. Cl.
| A61K 8/87 | (2006.01) |
| A45D 2/00 | (2006.01) |
| A45D 7/06 | (2006.01) |
| A61K 8/06 | (2006.01) |
| A61K 8/41 | (2006.01) |
| A61K 8/42 | (2006.01) |
| A61K 8/891 | (2006.01) |
| A61Q 5/02 | (2006.01) |
| A61Q 5/06 | (2006.01) |
| A61Q 5/12 | (2006.01) |

(52) U.S. Cl.
CPC ............... *A61K 8/87* (2013.01); *A45D 2/001* (2013.01); *A45D 7/06* (2013.01); *A61K 8/06* (2013.01); *A61K 8/416* (2013.01); *A61K 8/42* (2013.01); *A61K 8/891* (2013.01); *A61Q 5/02* (2013.01); *A61Q 5/06* (2013.01); *A61Q 5/12* (2013.01); *A61K 2800/48* (2013.01); *A61K 2800/884* (2013.01)

(58) Field of Classification Search
None
See application file for complete search history.

(56) References Cited

U.S. PATENT DOCUMENTS

| 5,951,969 | A | 9/1999 | Golinski et al. |
| 5,985,803 | A | 11/1999 | Rizvi et al. |
| 8,999,310 | B1 | 4/2015 | Frank et al. |
| 9,095,518 | B2 | 8/2015 | Pressly et al. |
| 9,326,926 | B2 | 5/2016 | Pressly et al. |
| 9,597,273 | B2 | 3/2017 | Pressly et al. |
| 2007/0020215 | A1 | 1/2007 | Mathonneau |
| 2007/0107142 | A1 | 5/2007 | Nguyen et al. |
| 2013/0149274 | A1 | 6/2013 | Nguyen et al. |
| 2014/0171354 | A1 | 6/2014 | Miralles et al. |
| 2015/0004117 | A1 | 1/2015 | Tan et al. |
| 2015/0004119 | A1 | 1/2015 | Tan et al. |
| 2015/0004124 | A1 | 1/2015 | Tan et al. |
| 2015/0034119 | A1 | 2/2015 | Pressly et al. |
| 2015/0037270 | A1 | 2/2015 | Pressly et al. |
| 2015/0037271 | A1 | 2/2015 | Pressly et al. |
| 2015/0290101 | A1 | 10/2015 | Pressly et al. |
| 2015/0328102 | A1 | 11/2015 | Pressly et al. |
| 2016/0175238 | A1 | 6/2016 | Shin et al. |
| 2016/0235649 | A1 | 8/2016 | Streuli |
| 2017/0119122 | A1* | 5/2017 | Rautenberg-Groth ... A45D 7/04 |

FOREIGN PATENT DOCUMENTS

| JP | 63154611 A | 6/1988 |
| JP | 2015086211 A | 5/2015 |
| WO | WO-0152005 A1 | 7/2001 |
| WO | WO-2016/100885 A1 | 6/2016 |

OTHER PUBLICATIONS

Anonymous: "Curly Hair Conditioner", Mintel, GNPF, 2015, pp. 1-2, XP002782449 (Year: 2015).*
Olaplex with relaxers, OLAPLEX™, pp. 1-2, Apr. 11, 2017, https://olaplex.es/olaplex-with-relaxers/.
Relaxers, Resource Library, Olaplex Education, pp. 1-2, Apr. 11, 2017, https://help.olaplex.com/detail/relaxers.
International Search Report and Written Opinion dated Oct. 25, 2018 for corresponding PCT Application No. PCT/US2018/034355.

* cited by examiner

*Primary Examiner* — Nannette Holloman
(74) *Attorney, Agent, or Firm* — Polsinelli PC

(57) ABSTRACT

The instant disclosure relates to methods for treating hair, for example, methods for imparting desirable cosmetic properties to the hair, especially hair treated with a chemical treatment composition. The methods include:
applying a hair-treatment composition to chemically treated hair, for example, within 30 minutes from when a chemical treatment composition is rinsed from the hair, the hair-treatment composition comprising:
one or more polyurethane latex polymers; and
rinsing the hair-treatment composition from the hair within 30 minutes from applying the hair-treatment composition to the hair.
After rinsing the hair-treatment composition from the hair, the hair may be subsequently dried and styled.

27 Claims, No Drawings

METHODS FOR TREATING CHEMICALLY TREATED HAIR

FIELD OF THE DISCLOSURE

The instant disclosure relates to methods for treating hair, especially chemically treated hair. The methods provide hair with a variety of desirable benefits, such as improved manageability, long-lasting style and frizz control, softness, and smoothness.

BACKGROUND

Many chemical treatments are available for changing the appearance of hair. For example, chemical treatments for permanently straightening or curling the hair are common. Also, hair may be lightened or bleached and oxidative dyes can be used to change the color of the hair. Chemical treatments are popular because their effects are long-lasting and can be drastic. Nonetheless, the biggest drawback to chemical treatments is the strain and damage caused to hair. This is because chemical treatments permanently change the chemical and physical structure of the hair. Chemical treatments can remove moisture from the surface of the hair cuticles resulting in the hair becoming brittle, dry, and more vulnerable to breakage.

Individuals seeking to change the shape of hair often turn to chemical procedures that use chemical relaxer compositions. Chemical relaxer compositions are often used on curly hair. The chemical relaxer compositions make hair easier to straighten by chemically "relaxing" the natural curls. The active agent is often a strong alkali, although some formulations are based on ammonium thioglycolate instead. Hair relaxer compositions are applied to hair at a salon by a professional or in the home by the individual consumer.

Hair fiber is a keratinous material, which is comprised of proteins (polypeptides). Many of the polypeptides in hair fibers are bonded together by disulfide bonds (—S—S—). A disulfide bond may be formed from the reaction of the two sulfhydryl groups (—SH), one on each of two cysteine residues, which results in the formation of a cystine residue. While there may be other types of bonds between the polypeptides in hair fibers, such as ionic salt bonds, the permanent curling and shape of the hair is essentially dependent on the disulfide bonds of cystine residues.

Chemical relaxing processes alter the aforementioned disulfide bonds between polypeptides in hair fibers to form lanthionine [S(CH$_2$ CHNH$_2$ COOH)$_2$]. Thus, the term "lanthionizing" is often used when referring to the relaxing or straightening of keratin fibers by hydroxide ions. Hair fibers may be relaxed or straightened by disrupting the disulfide bonds of the hair fibers with an alkaline agent or with a reducing agent. The chemical disruption of disulfide bonds with an alkaline agent is generally combined with mechanical straightening of the hair, such as combing, and straightening generally occurs due to changes in the relative positions of opposing polypeptide chains within the hair fiber. This reaction is generally terminated by rinsing and/or application of a neutralizing composition.

The reaction with the alkaline agent is normally initiated by hydroxide ions. Hair relaxing processes proceed via the release of the hydroxide ions, which penetrate the hair fiber and transform cystine residues to lanthionine residues. Chemical relaxer compositions often contain varying proportions of strong water-soluble bases, such as sodium hydroxide (NaOH), or include slightly-soluble metal hydroxides, such as calcium hydroxide (Ca(OH)$_2$), which can be converted in situ to soluble bases, such as guanidine hydroxide. Sodium hydroxide is extremely effective in straightening hair fibers but often causes a decrease in the strength of the hair fibers. Chemical relaxer composition often damage the hair to an extent and cause the hair to lose some of its desirable cosmetic properties such as shine, strength, smoothness, etc. Thus, mechanisms to reduce or prevent damage to hair and for improving the cosmetic properties of hair treated with chemical relaxer compositions are desired.

SUMMARY OF THE DISCLOSURE

The instant disclosure relates to methods for treating chemically treated hair, for example, methods for imparting desirable cosmetic properties to the hair, especially hair treated with a chemical relaxer composition. The disclosed methods compensate for damage to hair caused by chemical treatments including chemical relaxer treatments. Hair treated according to the disclosed methods exhibit improved style-control, strength, discipline, frizz control, smoothness, and softness. Furthermore, consumers find the natural look and feel of hair treated according to the methods to be very appealing.

The methods typically include:
  applying a hair-treatment composition to chemically treated hair, for example, within 30 minutes from when a chemical treatment composition is rinsed from the hair, the hair-treatment composition comprising:
    one or more polyurethane latex polymers; and
  rinsing the hair-treatment composition from the hair, for example, within 30 minutes from applying the hair-treatment composition to the hair.

After rinsing the hair-treatment composition from the hair, the hair may be subsequently dried and styled, for example, the hair may be dried with a blow dryer and/or styled with a hot iron.

The hair-treatment compositions may be applied individually to the hair and/or may be applied in combination with another composition, such as shampoo, a conditioner, a conditioning shampoo (all-in-one shampoo/conditioner), etc. In some cases, the hair-treatment composition may be combined with a shampoo that is applied to the hair and combined with a conditioner that is applied to the hair. The hair-treatment compositions may be combined with another composition prior to application to the hair or may be combined with another composition on the hair. For example, a hair-treatment composition may first be applied to the hair and without rinsing the hair-treatment composition from the hair, another composition (e.g., a conditioner, a conditioning shampoo, etc.) is applied to the hair, i.e., another composition is layered onto the underlying hair-treatment composition already on the hair. The order may be reversed. A composition such as a conditioner, a conditioning shampoo, etc., may first be applied to the hair, and without rinsing this composition from the hair, a hair-treatment composition is applied to the hair, i.e., a hair-treatment composition is layered onto the underlying composition already on the hair.

The hair-treatment compositions contain one or more polyurethane latex polymers. Many polyurethane latex polymers are known and useable in the hair-treatment compositions. Non-limiting examples include polyurethane-32, polyurethane-34, polyurethane-35, polyurethane-48, and a mixture thereof. The hair-treatment compositions typically combine the one or more polyurethane latex polymers with additional components such as one or more silicone-organic polymer hybrid compounds, for example, crotonic acid/vinyl C8-12 isoalkyl esters/VA/bis-vinyldimethicone crosspolymer, one or more thickening agents, or one or more bis-urea derivatives, for example, BIS-(C12-14 alkyl PPG-4) hexamethylenediurea. Additional components that are useful in the hair-treatment compositions include silicones, cationic polymers, fatty compounds, water-soluble solvents, emulsifiers, auxiliary agents, etc.

While not wishing to be bound by any particular theory, the inventors believe that when the hair-treatment compositions are applied shorly after a chemical treatment composition (e.g., a chemical relaxing composition) is rinsed from the hair the cuticles of the hair are open, thereby allowing components of the hair-treatment compositions to penetrate the hair fibers. Furthermore, it is believed that the methods provide the hair with a hydrophobic, flexible, film or film-like coating that is long-lasting, has a very natural look and feel, and improves the styling properties of the hair. The hydrophobic film or film-like coating also provides protection to the hair from damage, for example, damage caused by heat, environmental stress, etc. Furthermore, the film or film-like coating is long lasting, as it can survive repeated washings. Thus, hair maintains the desirable cosmetic properties imparted by the hair-treatment compositions despite subsequent shampooing, rinsing, etc.

Finally, as mentioned previously, the hair-treatment compositions are unique in their ability to provide hair with improved manageability, long-lasting style and frizz control, heat protection, and smoothness. Accordingly, the instant disclosure relates to methods for treating hair, for example, for improving the manageability of hair, for imparting lasting style and frizz control, for protecting the hair from damage including heat damage, and for imparting smoothness to the hair, etc.

DETAILED DESCRIPTION OF THE DISCLOSURE

The term "hair-treatment composition" encompasses many types of compositions for application to the hair, for example, chemical treatment compositions including chemical relaxer compositions, shampoos, conditioners, hair-rinses, hair lotions, hair gels, mouse-type products, sprays, etc. A hair-treatment composition is characterized by its ability to provide a cosmetic benefit to the hair. As is well-known, a shampoo provides cleansing benefits to the hair, a conditioner provides conditioning benefits to the hair, and gels can provide styling benefits to the hair. Non-limiting examples of additional benefits that can be imparted to hair include frizz control, smoothness, shine, ease of combability, fullness and body, strengthening, damage repair or resistance to damage, luster or color enhancement, protection from heat, etc.

The term "chemical treatment composition" encompasses compositions that include one or more active agents that chemically alter hair. An "active agent," in the context of the instant disclosure, relates to a compound, molecule, or combination of compounds/molecules that chemically changes hair. Active agents include, for example, oxidizing agents, reducing agents, non-reducing agents for shaping hair, agents for relaxing hair, dyeing agents, and mixtures thereof. Accordingly, depending on the nature of the active agent(s), the composition for chemically treating the hair may be a hair relaxing composition, a hair lightening or bleaching composition, a hair coloring composition, a hair curling (perming) composition, a hair straightening composition, an anti-frizz composition, a hair smoothing composition, a hair conditioning composition, etc.

Methods according to the instant disclosure include:
applying a hair-treatment composition to hair, for example, within 30 minutes from when a chemical treatment composition is rinsed from the hair, the hair-treatment composition comprising:
one or more polyurethane latex polymers; and
rinsing the hair-treatment composition from the hair, for example, within 30 minutes from applying the hair-treatment composition to the hair.

The methods are particularly useful for treating chemically relaxed hair. In some cases, the hair-treatment composition is applied to hair within 30 minutes from rinsing a chemical treatment composition from the hair, for example, while the hair is still wet or damp. The hair-treatment composition may be applied to the hair within about 30 minutes, 25 minutes, 20 minutes, 15 minutes, 10 minutes, 5 minutes, or 1 minute from rinsing a chemical treatment composition from the hair.

The hair-treatment composition may be applied individually to the hair and/or may be applied in combination with another composition, such as shampoo, a conditioner, a conditioning shampoo (all-in-one shampoo/conditioner), etc. In some cases, the hair-treatment composition may be combined with a shampoo that is applied to the hair and separately combined with a conditioner that is applied to the hair. The hair-treatment compositions may be combined with another composition prior to application to the hair or may be combined with another composition on the hair. For example, a hair-treatment composition may first be applied to the hair and without rinsing the hair-treatment composition from the hair, another composition (e.g., a conditioner, a conditioning shampoo, etc.) is applied to the hair, i.e., another composition is layered onto the underlying hair-treatment composition already on the hair. The order may be reversed. A composition such as a shampoo, a conditioner, a conditioning shampoo, etc., may first be applied to the hair, and without rinsing this composition from the hair, a hair-treatment composition is applied to the hair, i.e., a hair-treatment composition is layered onto the underlying composition already on the hair.

As noted above, the hair-treatment compositions may be applied to the hair independently or may be combined or layered with other compositions. After application, the hair-treatment composition (or the combination of hair-treatment composition with another composition) may be allowed to remain on the hair for a period of time, although allowing the hair-treatment composition or combination to remain on the hair for an extended period of time is not necessary. For instance, the hair-treatment composition or combination may be allowed to remain on the hair for about 10 seconds to about 30 minutes, from about 10 seconds to about 25 minutes, from about 10 seconds to about 20 minutes, from about 10 seconds to about 15 minutes, from about 10 seconds to about 10 minutes, or from about 10 seconds to about 5 minutes. After the hair-treatment composition is rinsed from the hair, the hair may be styled. For example, the hair may be blow dried and optionally further treated with a hot iron (e.g., a flat iron, a curling iron, etc.). Typically, the hair is dried and/or styled within 30 minutes from rinsing the hair-treatment composition from the hair. The hair may be dried and/or styled within 25, 20, 15, 10, or 5 minutes from when the hair-treatment composition is rinsed from the hair.

In some instances, one or more hair-treatment compositions are combined with both a shampoo and a conditioner. The combination with the shampoo is applied first to the hair and rinsed. The combination with the conditioner is applied second to the hair and rinsed. Then, the hair may be dried and/or styled. The hair-treatment composition may also individually be applied to the hair before the mixture with shampoo is applied to the hair, after the mixture with shampoo is rinsed from the hair but before the mixture with conditioner is applied to the hair, and/or after the mixture with conditioner is rinsed from the hair. The hair-treatment composition can be easily mixed with other composition in the hands immediately prior to application to the hair.

When combining a hair-treatment composition with another composition such as a shampoo, conditioner, conditioning shampoo, etc., the ratio of hair-treatment composition to the other composition may be about 1:5 to about 5:1 (hair treatment composition:shampoo, conditioner, or conditioning shampoo, etc.). Likewise, in some cases, the ratio may be about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1.

In some cases, the methods include layering the hair-treatment composition with another composition. For example, in one embodiment, the methods include: applying a hair-treatment composition according to the instant disclosure to the hair; applying a shampoo, a conditioner, or a conditioning shampoo, etc., to the hair before rinsing the hair-treatment composition from the hair; and rinsing the combination of hair-treatment composition and shampoo, conditioner, or conditioning shampoo, etc., from the hair together. After rinsing, the hair may also be dried and/or styled.

Alternatively, in another embodiment, the methods include: applying a shampoo, conditioner, or conditioning shampoo, etc., to the hair before applying a hair-treatment composition to the hair; without rinsing the shampoo, conditioner, or conditioning shampoo, etc., from the hair, applying the hair-treatment composition according to the instant disclosure to the hair; and rinsing the combination of hair-treatment composition and the shampoo, conditioner, or conditioning shampoo from the hair together. After rinsing, the hair may also be dried and/or styled.

The methods may also include application of a chemical treatment composition to hair and chemically treating the hair prior to applying a hair-treatment composition, shampoo, conditioner, and/or conditioning shampoo to the chemically treated hair. A non-limiting example of a method according to the instant disclosure includes:
  applying a chemical treatment composition, for example a chemical relaxing composition, to hair and chemically treating the hair;
  rinsing the chemical treatment composition from the hair;
  combining a hair-treatment composition with a shampoo and applying the hair-treatment composition and shampoo to the hair within 30 minutes from rinsing the chemical treatment composition from the hair;
  rinsing the hair-treatment composition and shampoo from the hair together within 30 minutes of applying the hair-treatment composition and shampoo to the hair;
  combining a hair-treatment composition with a conditioner and applying the hair-treatment composition and conditioner to the hair within 30 minutes of rinsing the hair-treatment composition and shampoo from the hair;
  rinsing the hair-treatment composition and conditioner from the hair within 30 minutes of applying the hair-treatment composition and the conditioner to the hair; and
  styling the hair.

The methods described throughout the disclosure are unique in their ability to provide hair with improved manageability, long-lasting style and frizz control, heat protection, and smoothness. Accordingly, the instant disclosure relates to methods for treating hair, for example, for improving the manageability of hair, for imparting lasting style and frizz control, for protecting the hair from damage including heat damage, and for imparting smoothness to the hair, etc.

The hair-treatment compositions discussed throughout the disclosure typically contain one or more polyurethane latex polymers. Many polyurethane latex polymers are known and useable in the hair-treatment compositions. Non-limiting examples include polyurethane-32, polyurethane-34, polyurethane-35, polyurethane-48, and a mixture thereof. The hair-treatment compositions typically combine the one or more polyurethane latex polymers with additional components such as one or more silicone-organic polymer hybrid compounds, for example, crotonic acid/vinyl C8-12 isoalkyl esters/VA/bis-vinyldimethicone crosspolymer, one or more thickening agents, and/or one or more one or more bis-urea derivatives, for example, BIS-(C12-14 alkyl PPG-4) hexamethylenediurea. Additional components that are useful in the hair-treatment compositions include silicones, cationic polymers, fatty compounds, water-soluble solvents, emulsifiers, auxiliary agents, etc.

As mentioned previously, chemical treatment compositions include one or more active agents. For example, an active agent may reduce disulfide bonds, reestablish or form disulfide bonds, remove melanin from the hair, covalently bond to the hair, etc. Non-limiting examples of active agents include oxidizing agents, reducing agents, non-reducing agents for shaping hair, relaxing agents, dyeing agents, and mixtures thereof. Based on the type of active agent, the composition for chemically treating hair may be a hair lightening or bleaching composition, hair coloring composition, a hair perming or straightening composition, a hair relaxing composition, or a mixture thereof.

Hair lightening compositions typically include one or more oxidizing agents. Non-limiting examples of oxidizing agents include peroxides, persulfates, perborates, percarbonates, and mixtures thereof. In some cases, the hair lightening composition includes one or more persulfates, such as those selected from the group consisting of sodium persulfate, potassium persulfate, ammonium persulfate, and mixtures thereof. In some cases, the hair lightening compositions include peroxide, such as hydrogen peroxide.

Hair perming or straightening compositions typically include one or more reducing agents. Non-limiting examples of reducing agents include cysteine or a derivative of cysteine, cysteamine or a derivative of cysteamine, thiolactic acid or an ester of thiolactic acid, thioglycolic acid or an ester of thioglycolic acid, thioglycerol, and mixtures thereof. In some cases, the reducing agent is a glyceryl or glycol monothioglycolate, diammonium dithiodiglycolate, ammonium thioglycolate, or a mixture thereof.

Hair straightening or relaxing compositions may include one or more non-reducing agents for shaping hair. Non-reducing agents for shaping hair may be one or more hydroxide compounds, non-hydroxide compounds, or mixtures thereof. For instance, the hydroxide compounds may be alkali metal hydroxides, alkaline-earth metal hydroxides, transition metal hydroxides, and mixtures thereof. Non-limiting examples include of hydroxide compounds include sodium hydroxide, potassium hydroxide, lithium hydroxide, calcium hydroxide, magnesium hydroxide, barium hydroxide, strontium hydroxide, manganese hydroxide, zinc hydroxide, guanidine hydroxide, and mixtures thereof.

The non-hydroxide compounds may include one or more ethyleneamines, alkanolamines, amino acids, or mixtures thereof. Non-limiting examples of non-hydroxide compounds include ethylenediamine, monoethanolamine, diethanolamine, propanolamine, isopropanolamine, triethanolamine, butanolamine, isobutanolamine, methylethanolamine, butylethanolamine, arginine, lysine, and mixtures thereof.

In some cases, when the compositions include hydrogen peroxide as an active agent, the composition further comprises a second oxidizing agent other than hydrogen peroxide and/or the compositions includes an oxidative dye precursor. For example, in some cases the second oxidizing agent is a persulfate. Non-limiting examples of persulfates include potassium persulfate, sodium persulfate, ammonium persulfate, and mixtures thereof.

Hair coloring or dyeing compositions typically include one or more colorants or dyeing agents. Non-limiting examples of colorants or dyeing agents include direct dyes, oxidative dyes, direct action dyes, natural dyes, metallic dyes, reactive dyes, and mixtures thereof.

Non-limiting examples of various hair-treatment compositions comprising one or more polyurethane latex polymers are provided below.

Hair-Treatment Composition with Polyurethane Latex Polymer and Cationic Emulsifiers In some cases, the hair-treatment compositions include one or more polyurethane latex polymers and one or more cationic emulsifiers. For example, the hair-treatment composition may include:
one or more polyurethane latex polymers;
one or more cationic emulsifiers;
one or more fatty compounds; and
water.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

Many cationic emulsifiers and/or surfactants are well-known and may be used in the hair-treatment compositions. Non-limiting examples of cationic emulsifiers and/or surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, myristamidopropyl PG-dimonium chloride phosphate, brassicyl isoleucinate esylate, and a mixture thereof. In some cases, the one or more cationic emulsifiers and/or surfactants may be selected from the group consisting of brassicyl isoleucinate esylate, behentrimonium chloride, and a mixture thereof. A more exhaustive list of cationic emulsifiers and/or surfactants that may be included in the hair-treatment compositions is provided later, under the heading "Cationic Emulsifiers and/or Surfactants."

The total amount of the one or more cationic emulsifiers and/or surfactants may vary but are typically about 0.01 to about 10 wt. %, based on the total weight of the hair-treatment composition. In some case, the total amount of the one or more cationic emulsifiers and/or surfactants may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

One or more fatty compounds are typically included in the hair-treatment compositions. Non-limiting examples of fatty compounds include oils, mineral oil, waxes, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, undecane, tridecane, 2-oleamido-1,3-octadecanediol (ceramide), and a mixture thereof. Additionally, in some cases, the one or more fatty compounds may be selected from the group consisting of brassica alcohol, cetyl esters, octyldodecanol, cetearyl alcohol, sunflower seed oil, isostearyl alcohol, and a mixture thereof. A more exhaustive list of fatty compounds that may be included in the hair-treatment compositions is provided later, under the heading "Fatty Compounds."

The total amount of the one or more fatty compounds can vary but is typically about 1 to about 40 wt. %, based on the total weight of the hair-treatment composition. In some cases, the total amount of the one or more fatty compounds may be about 0.5 to about 30 wt. %, about 0.5 to about 25 wt. %, about 0.5 to about 20 wt. %, about 0.5 to about 15 wt. %, about 0.5 to about 10 wt. %, about 1 to about 30 wt. %, about 1 to about 25 wt. %, about 1 to about 20 wt. %, about 1 to about 15 wt. %, or about 1 to about 10 wt. %.

In some cases, the hair-treatment compositions may include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, propylene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

A more exhaustive list of water-soluble solvents that may be included in the hair-treatment compositions is provided later, under the heading "Water-Soluble Solvents."

The total amount of the one or more water-soluble solvents (which is separate than the water in the compositions) may vary, but in some cases are about 0.1 to about 25 wt. %, based on the total weight of the hair-treatment composition. The total amount of the one or more water-soluble solvents may be about 0.1 to about 20 wt. %, 0.1 to about 15 wt. %, 0.1 to about 10 wt. %, about 0.1 to about 5 wt. %, about 0.5 to about 25 wt. %, about 0.5 to about 20 wt. %, about 0.5 to about 15 wt. %, about 0.5 to about 10 wt. %, or about 0.5 to about 5 wt. %.

One or more silicones may be included in the hair-treatment compositions. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. For example, in some cases, the hair-treatment compositions may include dimethicone, lauryl PEG/PPG-18/18 methicone, dimethiconol, amodimethicone, cyclomethicone, and a mixture thereof. A more exhaustive list of silicones that may be included in the hair-treatment compositions is provided later, under the heading "Silicones."

The total amount of the one or more silicones may vary but is typically about 0.01 to about 20 wt. %, based on the total weight of the hair-treatment composition. In some cases, the total amount of the one or more silicones is about 0.01 to about 15 wt. %, 0.01 to about 10 wt. %, about 0.01 to about 8 wt. %, about 0.01 to about 5 wt. %, about 0.1 to about 20 wt. %, about 0.1 to about 15 wt. %, about 0.1 to about 10 wt. %, or about 0.1 to about 5 wt. %.

One or more emulsifiers other than the one or more cationic emulsifiers may be included in the hair-treatment compositions. For example the emulsifier may be an amphoteric, anionic, or nonionic emulsifier, used alone or as a mixture, and optionally with a co-emulsifier. The emulsifiers are chosen in an appropriate manner according to the emulsion to be obtained. In some cases, the one or more emulsifiers (other than the cationic emulsifiers) may include ethoxylated fatty alcohols, ethoxylated fatty acids, partial glycerides of ethoxylated fatty acids, polyglycerolated fatty acid triglycerides and their ethoxylated derivatives, and a mixture thereof.

Non-limiting examples of nonionic emulsifiers include polyol esters, a glycerol ethers, oxyethylenated and/or oxypropylenated ethers, ethylene glycol polymers, and mixtures thereof. For example, in some cases the emulsifier includes a mixture of a polyol ester and an ethylene glycol polymer, for example, a mixture of glyceryl stearate and PEG-100 stearate. In some instances, an oxyalkylenated organosiloxane emulsifier is included. Non-limiting examples include dimethicone/PEG-10/15 crosspolymer, PEG-15 lauryl dimethicone crosspolymer, PEG-15 lauryl dimethicone crosspolymer, PEG-10 lauryl dimethicone crosspolymer, or a mixture thereof.

In some instance, the one or more emulsifiers include an organosiloxane emulsifier, including crosslinked organosiloxane emulsifiers. For example, one or more emulsifiers selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In some cases, the emulsifiers may be one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

In some instances, the hair-treatment compositions may include beheneth-10, PPG-3 benzyl ether ethylhexanoate, or a mixture thereof.

A more exhaustive list of emulsifiers that may be included in the hair-treatment compositions is provided later, under the heading "Emulsifiers."

The total amount of the one or more emulsifiers (other than the one or more cationic emulsifier and/or surfactants) may vary but is typically about 1 to about 15 wt. %, based on the total weight of the hair-treatment composition. The total amount of the one or more emulsifiers may be about 0.1 to about 10 wt. %, about 0.1 to about 8 wt. %, about 0.1 to about 6 wt. %, about 0.1 to about 5 wt. %, 1 to about 10 wt. %, about 1 to about 8 wt. %, about 1 to about 6 wt. %, or about 1 to about 5 wt. %.

Cationic polymers may also be useful in certain hair-treatment compositions of the instant disclosure. Non-limiting examples of cationic polymers include poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, the hair-treatment compositions include one or more polyquaternium polymers. A more exhaustive list of cationic polymers that may be included in the hair-treatment compositions is provided later, under the heading "Cationic Polymers."

The total amount of the one or more cationic polymers may vary but is typically about 0.01 to about 10 wt. %, based on the total amount of the hair-treatment composition. The total amount of the one or more cationic polymers may be about 0.01 to about 8 wt. %, about 0.01 to about 6 wt. %, about 0.01 to about 4 wt. %, about 0.05 to about 10 wt. %, about 0.05 to about 8 wt. %, about 0.05 to about 6 wt. %, about 0.05 to about 4 wt. %, about 0.1 to about 10 wt. %, about 0.1 to about 8 wt. %, about 0.1 to about 6 wt. %, or about 0.1 to about 4 wt. %.

One or more amino acids and/or amino sulfonic acids, and/or a salt thereof, may be incorporated into the hair-treatment compositions. Non-limiting examples of amino acids and/or sulfonic acids, and/or a salt thereof include arginine, aspartic acid, cysteine, glycine, lysine, methionine, proline, tyrosine, phenylalanine, carnitine, taurine, betaine, a salt thereof, and a mixture thereof. In some cases, charged amino acids may be used. Non-limiting examples of charged amino acids include arginine, lysine, aspartic acid, and glutamic acid. In some cases, polar amino acids are useful. Non-limiting examples of polar amino acids include glutamine, asparagine, histidine, serine, threonine, tyrosine, cysteine, methionine, and tryptophan.

The total amount of the one or more amino acids and/or amino sulfonic acids, and/or a salt thereof may vary but is typically about 0.001 to about 5 wt. %, about 0.001 to about 4 wt. %, about 0.001 to about 3 wt. %, about 0.001 to about 2 wt. %, 0.01 to about 5 wt. %, about 0.01 to about 4 wt. %, about 0.01 to about 3 wt. %, or about 0.01 to about 2 wt. %, based on the total weight of the hair-treatment composition.

The hair-treatment compositions may contain one or more thickeners (also referred to as thickening agents or viscosity modifying agents). Classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition. In some cases, associative thickening polymers may be useful in anionic surfactant-free hair-treatment compositions, in particular, anionic surfactant free conditioning shampoos. For example, the anionic surfactant-free conditioning shampoos may include one or more anionic associative polymers.

The total amount of the one or more thickening agents may vary, but in some cases is about 0.1 to about 15 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about wt. %, about 0.5 to about 5 wt. %, about 1 to about 10 wt. %, about 1 to about 8 wt. %, about 1 to about 6 wt. %, or about 1 to about 5 wt. %, based on the total weight of the composition.

One or more preservatives may be included in the hair-treatment compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid (EDTA), potassium sorbate, and/or grapefruit seed extract, or a mixture thereof. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), and a mixture thereof. In some cases, the hair-treatment compositions may include one or more preservatives selected from the group consisting of sodium benzoate, benzoic acid, chlorhexidine digluconate, chlorhexidine dihydrochloride, salicylic acid, phenoxyethanol, methyl paraben, and a mixture thereof.

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

In one embodiment, the hair-treatment compositions of the instant case relate to emulsions (e.g., oil-in-water emulsions and water-in-oil emulsions), which include:
 about 0.01 to about 10 wt. % of polyurethane-34;
 about 0.01 to about 10 wt. % of one or more cationic emulsifiers and/or surfactants;
 about 1 to about 20 wt. % of one or more fatty compounds;
 about 0.1 to about 10 wt. %, one or more water-soluble solvents; and
 about 50 to about 95 wt. % of water.

More specifically, the hair-treatment compositions may include:
 about 0.01 to about 10 wt. % of polyurethane-34;
 about 0.01 to about 10 wt. % of one or more cationic emulsifiers and/or surfactants selected from the group consisting of cetrimonium chloride, stearimonium chloride, behentrimonium chloride, behentrimonium methosulfate, behenamidopropyltrimonium methosulfate, stearamidopropyltrimonium chloride, myristamidopropyl PG-dimonium chloride phosphate, brassicyl isoleucinate esylate, and a mixture thereof;
 about 1 to about 20 wt. % of one or more fatty compounds selected from the group consisting of oils, alkanes, fatty alcohols, fatty acids, fatty alcohol derivatives, fatty acid derivatives, esters of fatty alcohols, hydroxy-substituted fatty acids, waxes, and a mixture thereof;
 about 0.1 to about 10 wt. %, one or more water-soluble solvents polyhydric alcohols, glycol ethers, $C_{1-4}$ alcohols, and a mixture thereof; and about 50 to about 95 wt. % of water.

The hair-treatment compositions above may further optionally include:
 about 0.01 to about 10 wt. % of one or more silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof; and/or
 about 1 to about 10 wt. % of one or more emulsifiers that is different than the one or more cationic emulsifiers and/or surfactants are selected from the group consisting of ethoxylated fatty alcohols, ethoxylated fatty acids, partial glycerides of ethoxylated fatty acids, polyglycerolated fatty acid triglycerides and their ethoxylated derivatives, and a mixture thereof.

In some instances, hair-treatment compositions according to the instant disclosure include:
 about 0.01 to about 5 wt. % of polyurethane-34;
 about 0.01 to about 5 wt. % of one or more cationic emulsifiers and/or surfactants selected from the group consisting of cetrimonium chloride, stearimonium chloride, behentrimonium chloride, behentrimonium methosulfate, behenamidopropyltrimonium methosulfate, stearamidopropyltrimonium chloride, myristamidopropyl PG-dimonium chloride phosphate, brassicyl isoleucinate esylate, and a mixture thereof, preferably, brassicyl isoleucinate esylate, behentrimonium chloride, and a mixture thereof;
 about 1 to about 10 wt. % of one or more fatty compounds selected from the group consisting of cetyl esters, isostearyl alcohol, cetearyl alcohol, brassica alcohol, octyldodecanol, oil (e.g., mineral oil, sunflower oil, etc.);
 about 0.1 to about 10 wt. %, one or more water-soluble solvents polyhydric alcohols, glycol ethers, $C_{1-4}$ alcohols, and a mixture thereof, preferably, glycerin and/or isopropyl alcohol;
 about 1 to about 10 wt. % of one or more emulsifiers that is different than the one or more cationic emulsifiers and/or surfactants are selected from the group consisting of ethoxylated fatty alcohols, ethoxylated fatty acids, partial glycerides of ethoxylated fatty acids, polyglycerolated fatty acid triglycerides and their ethoxylated derivatives, and a mixture thereof, preferably, beheneth-10, PPG-3 benzyl ether ethylhexanoate, and a mixture thereof;
 about 70 to about 95 wt. % of water.

The hair-treatment compositions above may further optionally include:
 about 0.01 to about 10 wt. % of one or more silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof; and/or
 about 0.1 to about 5 wt. % of one or more cationic polymers, preferably one or more polyquaterniums such as polyquaternium-11, polyquaternium-72, and a mixture thereof.

The types of hair-treatment compositions discussed above are described in detail in U.S. Ser. No. 15/582,076, which is incorporated herein by reference in its entirety.

Hair-Treatment Composition with Polyurethane Latex Polymer and Thickening Agent In some cases, the hair-treatment compositions include one or more polyurethane latex polymers and one or more thickening agents. For example, the hair-treatment composition may include:
- one or more polyurethane latex polymers;
- one or more thickening agents;
- one or more water soluble solvents; and
- water.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

Non-limiting examples of thickening agents that may be used in the hair-treatment compositions include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof. In some cases, the one or more thicking agents are selected from the group consisting of cross linked acrylic acid polymers (carbomer), methyl cellulose, ethyl cellulose, hydroxyethyl cellulose, hydroxypropyl methyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof.

The total amount of the one or more thickening agents can vary but is typically about 0.01 to about 10 wt. %, based on the total weight of the hair-treatment composition. The total amount of the one or more thickening agents may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

The hair-treatment compositions may include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, proplene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

A more exhaustive list of water-soluble solvents that may be included in the hair-treatment compositions is provided later, under the heading "Water-Soluble Solvents."

The total amount of the one or more water-soluble solvents (which is separate than the water in the compositions) may vary, but in some cases are about 0.1 to about 60 wt. %, based on the total weight of the hair-treatment composition. The total amount of the one or more water-soluble solvents may be about 0.1 to about 55 wt. %, about 0.1 to about 50 wt. %, about 0.1 to about 45 wt. %, about 0.1 to about 60 wt. %, about 0.1 to about 55 wt. %, about 0.1 to about 50 wt. %, about 0.1 to about 50 wt. %, about 1 to about 60 wt. %, about 1 to about 55 wt. %, about 1 to about 50 wt. %, about 5 to about 60 wt. %, about 5 to about 55 wt. %, about 10 to about 50 wt. %, or about 0.1 to about 10 wt. %, about 0.1 to about 5 wt. %.

One or more silicones may be included in the hair-treatment compositions. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. For example, in some cases, the hair-treatment compositions may include dimethicone, lauryl PEG/PPG-18/18 methicone, dimethiconol, amodimethicone, cyclomethicone, and a mixture thereof. A more exhaustive list of silicones that may be included in the hair-treatment compositions is provided later, under the heading "Silicones."

The total amount of the one or more silicones may vary but is typically about 0.01 to about 40 wt. %, based on the total weight of the hair-treatment composition. In some cases, the total amount of the one or more silicones is about 0.01 to about 30 wt. %, about 0.01 to about 20 wt. %, about 0.01 to about 15 wt. %, 0.01 to about 10 wt. %, about 0.01 to about 8 wt. %, about 0.01 to about 5 wt. %, about 0.1 to about 40 wt. %, about 0.1 to about 30 wt. %, about 0.1 to about 20 wt. %, about 0.1 to about 15 wt. %, about 0.1 to about 10 wt. %, or about 0.1 to about 5 wt. %.

The above hair-treatment compositions may be in a variety of different forms, for example, a gel, a lotion, a cream, an aerated product (e.g., a mousse), etc. For example, in a specific embodiment, the hair-treatment composition is a gel comprising:

about 0.01 to about 10 wt. %, about 0.1 to about 10 wt. %, or about 1 to about 5 wt. % of polyurethane-34;
about 0.01 to about 10 wt. %, about 0.1 to about 8 wt. %, or about 0.1 to about 5 wt. % of one or more thickening agents, for example, one or more thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;

about 0.01 to about 60 wt. %, about 0.1 to about 55 wt. %, or about 0.1 to about 50 wt. % of one or more water-soluble solvents, for example, one or more water-soluble solvents are selected from the group consisting of polyhydric alcohols, glycol ethers, $C_{1-4}$ alcohols, and a mixture thereof;
optionally, about 0.01 to about 30 wt. %, about 1 to about 25 wt. %, or about 5 to about 25 wt. % of one or more silicones, for example, silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof; and
about 15 to about 90 wt. % of water.

In one embodiment, the hair-treatment compositions include:
one or more polyurethane latex polymers;
one or more thickening agents;
one or more emulsifiers;
one or more fatty compounds; and
water.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

Non-limiting examples of thickening agents that may be used in the hair-treatment compositions include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof. In some cases, the one or more thicking agents are selected from the group consisting of cross linked acrylic acid polymers (carbomer), methyl cellulose, ethyl cellulose, hydroxyethyl cellulose, hydroxypropyl methyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof.

The total amount of the one or more thickening agents can vary but is typically about 0.01 to about 10 wt. %, based on the total weight of the hair-treatment composition. The total amount of the one or more thickening agents may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

These hair-treatment compositions include one or more emulsifiers (and are often in the form of an emulsion). Non-limiting examples of emulsifiers include alkylpolyglycosides, glyceryl esters, ethylene glycol esters, propylene glycol esters and sucrose esters of fatty acids, ethoxylated fatty alcohols, ethoxylated fatty acids, partial glycerides of ethoxylated fatty acids, polyglycerolated fatty acid triglycerides and their ethoxylated derivatives, and a mixture thereof. In some cases, alkylpolyglycosides are useful, in particular octyldodecyl xyloside, cetearyl glucoside, isostearyl glucoside, and mixtures thereof. Alkylpolyglucosides may be used with a coemulsifier, more especially with a fatty alcohol and/or a fatty acid (fatty compounds of the instant disclosure) and especially a fatty alcohol containing the same fatty chain as that of the alkylpolyglucoside, i.e. comprising from 14 to 24 carbon atoms and containing a branched and/or unsaturated chain, for example isostearyl alcohol when the alkylpolyglucoside is isostearyl glucoside, and oleyl alcohol when the alkylpolyglucoside is oleyl glucoside, and octyldodecanol when the alkylpolyglucoside is octyldodecyl xyloside.

In some cases, nonionic emulsifiers may be used. Non-limiting examples of nonionic emulsifiers include glyceryl esters, ethylene glycol esters, propylene glycol esters and sucrose esters of fatty acids, such as: glyceryl caprate, glyceryl lanolate, glyceryl myristate, glyceryl laurate, glyceryl dilaurate, glyceryl monostearate, glyceryl monohydroxy stearate, glyceryl stearate, glyceryl stearate citrate, glycol stearate, glycol distearate, glycol dilaurate, diethylene glycol dilaurate, propylene glycol stearate, propylene glycol laurate, propylene glycol distearate, palm glycerides, hydrogenated coco glycerides, sucrose distearate, and a mixture thereof. Another useful class of non-ionic emulsifiers is polyethylene esters of fatty acids, fatty acid glycerides and sorbitan esters and with ethylene groups ranging from 5 to 150. Examples include: PEG-8 stearate, PEG-9 stearate, PEG-8 distearate, PEG-20 stearate, PEG-30 stearate, PEG-40 stearate, EG-50 stearate, PEG-100 stearate, PEG-150 laurate, PEG-30 glyceryl stearate, PEG-25 glyceryl trioleate, PEG-15 glyceryl ricinoleate, PEG-20 glyceryl stearate, PEG-20 glyceryl isostearate, PEG-20 glyceryl oleate, PEG-20 glyceryl laurate, PEG-30 stearate, PEG-30 glyceryl stearate, PEG-40 sorbitan lanolate, PEG-6 sorbitan beeswax, PEG-20 sorbitan beeswax, and a mixture thereof. Yet another useful class of non-ionic emulsifiers is represented by ethoxylated fatty alcohols with ethylene groups ranging from 2 to 30. Other nonionic emulsifiers may include sorbitan monoesters like sorbitan stearate, sorbitan tristearate, sorbitan palmitate, sorbitan laurate, cholesterol, lanolin, phytosterols, lecithin and hydrogenated lecithin.

A more exhaustive list of emulsifiers that may be included in the hair-treatment compositions is provided later, under the heading "Emulsifiers."

The total amount of the one or more emulsifiers can vary but is typically about 0.1 to about 15 wt. %, based on the total weight of the hair-treatment composition. In some cases, the total amount of the one or more emulsifiers may be about 0.1 to about 12 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 5 wt. %, or about 1 to about 5 wt. %.

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of C13-16 isoparaffin, PEG-40 hydrogenated castor oil, isononyl isononoanoate, hydrogenated polyisobutene, beeswax, shea butter, cetearyl alcohol, cetyl esters, isononanoate, and a mixture thereof.

A more exhaustive list of fatty compounds that may be included in the hair-treatment compositions is provided later, under the heading "Fatty Compounds."

The total amount of the one or more fatty compounds can vary but is typically about 1 to about 40 wt. %, based on the total weight of the hair-treatment composition. In some cases, the total amount of the one or more fatty compounds may be about 0.5 to about 30 wt. %, about 0.5 to about 25 wt. %, about 0.5 to about 20 wt. %, about 0.5 to about 15 wt. %, about 0.5 to about 10 wt. %, about 1 to about 30 wt. %, about 1 to about 25 wt. %, about 1 to about 20 wt. %, about 1 to about 15 wt. %, or about 1 to about 10 wt. %.

In a more specific embodiment, the hair-treatment composition is an emulsion comprising:
  about 0.01 to about 10 wt. %, about 0.1 to about 10 wt. %, or about 1 to about 5 wt. % of polyurethane-34;
  about 0.01 to about 10 wt. %, about 0.1 to about 8 wt. %, or about 0.1 to about 5 wt. % of one or more thickening agents, for example, thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
  about 0.1 to about 15 wt. %, about 0.1 to 10, or about 0.1 to about 8 wt. % of one or more emulsifiers selected from the group consisting of alkylpolyglycosides, glyceryl esters, ethylene glycol esters, propylene glycol esters and sucrose esters of fatty acids, ethoxylated fatty alcohols, ethoxylated fatty acids, partial glycerides of ethoxylated fatty acids, polyglycerolated fatty acid triglycerides, and a mixture thereof;
  about 1 to about 40 wt. %, about 1 to about 30 wt. %, or about 1 to about 20 wt. % of one or more fatty compounds, for example, fatty compounds selected from the group consisting of C13-14 isoparaffin, isononyl isonanoate, hydrogenated polyisobutene, shea butter, cetearyl alcohol, cetyl esters, isononanoat, and a mixture thereof; and
  water.

In some instances, the hair-treatment composition is a water-in-oil emulsion. Emulsifiers appropriate for use in water-in-oil emulsions are described throughout the instant disclosure. Nonetheless, in some cases, a water-in-oil emulsion includes one or more alkylpolyglycosides. A particularly well suited alkylpolyglycoside for use in water-in-oil emulsions comprising high amounts of an aqueous phase is octyldodecyl xyloside. This emulsifier may be used with a coemulsifer, such as octyldodecanol (a fatty compound). A more exhaustive list of emulsifiers that may be included in the water-in-oil emulsions is provided later, under the heading "Emulsifiers."

The total amount of water in these water-in-oil emulsions can vary but is typically about 60 wt. % to about 90 wt. %, based on the total weight of the hair-treatment composition. The total amount of water may be about 65 wt. % to about 90 wt. %, about 70 wt. % to about 90 wt. %, about 60 to about 85 wt. %, about 65 to about 85 wt. %, or about 70 to about 85 wt. %.

A non-limiting embodiment of a water-in-oil emulsion includes:
  about 0.01 to about 10, about 0.1 to about 10, or about 0.1 to about 5 wt. % of polyurethane-34;
  about 0.01 to about 10 wt. %, about 0.1 to about 8 wt. %, or about 0.1 to about 5 wt. % of one or more thickening agents selected from the group consisting of selected from the group consisting of polyacrylamide, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
  about 0.1 to about 10 wt. %, about 0.1 to about 8 wt. %, or about 0.1 to about 5 wt. % of one or more emulsifiers, wherein the one or more emulsifiers comprise one or more alkylpolyglycosides, in particular octyldodecyl xyloside;
  about 1 to about 40 wt. %, about 1 to about 30, or about 5 to about 25 wt. % of one or more fatty compounds selected from the group consisting of C13-14 isoparaffin, isononyl isonanoate, hydrogenated polyisobutene, shea butter, cetearyl alcohol, and cetyl esters, isononanoate, and a mixture thereof; and
  about 60 wt. % to about 90 wt. %, about 65 to about 90 wt. %, or about 70 to about 90 wt. % of water.

In some instances, the hair-treatment composition is an oil-in-water emulsion. Non-limiting examples of emulsifiers that may be used in oil-in-water emulsions are provided throughout the disclosure. Nonetheless, non-limiting examples include alkylpolyglycosides, glyceryl esters, ethylene glycol esters, propylene glycol esters and sucrose esters of fatty acids, ethoxylated fatty alcohols, ethoxylated fatty acids, partial glycerides of ethoxylated fatty acids, polyglycerolated fatty acid triglycerides and their ethoxylated derivatives, and a mixture thereof. A more exhaustive list of emulsifiers that may be included in the oil-in-water compositions is provided later, under the heading "Emulsifiers."

The total amount of water in these water-in-oil emulsions can vary but is typically about 50 wt. % to about 80 wt. %, based on the total weight of the hair-treatment composition. The total amount of water may be about 55 wt. % to about 80 wt. %, about 60 wt. % to about 80 wt. %, about 50 to about 85 wt. %, about 55 to about 85 wt. %, or about 60 to about 80 wt. %.

A non-limiting embodiment of an oil-in-water emulsion includes:
  about 0.01 to about 10, about 0.1 to about 10, or about 0.1 to about 5 wt. % of polyurethane-34;
  about 0.01 to about 10 wt. %, about 0.1 to about 8 wt. %, or about 0.1 to about 5 wt. % of one or more thickening agents selected from the group consisting of selected from the group consisting of polyacrylamide, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
  about 0.1 to about 10 wt. %, about 0.1 to about 8 wt. %, or about 0.1 to about 5 wt. % of one or more emulsifiers selected from the group consisting of glyceryl stearate, cetearyl glucoside, and a mixture thereof;
  about 1 to about 40 wt. % of one or more fatty compounds selected from the group consisting of C13-14 isoparaffin, isononyl isonanoate, hydrogenated polyisobutene, shea butter, cetearyl alcohol, and cetyl esters, and a mixture thereof; and
  about 50 wt. % to about 80 wt. % of water.

In one embodiment, the hair-treatment compositions include:
  one or more polyurethane latex polymers;
  one or more thickening agents;
  one or more amphoteric surfactants; and
  water.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

Non-limiting examples of thickening agents that may be used in the hair-treatment compositions include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof. In some cases, the one or more thicking agents are selected from the group consisting of cross linked acrylic acid polymers (carbomer), methyl cellulose, ethyl cellulose, hydroxyethyl cellulose, hydroxypropyl methyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof. A more exhaustive list of thickening agents that may be included in the hair-treatment compositions is provided later, under the heading "Thickening Agents."

The total amount of the one or more thickening agents can vary but is typically about 0.01 to about 10 wt. %, based on the total weight of the hair-treatment composition. The total amount of the one or more thickening agents may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

Amphoteric surfactants are well-known and may be used in the instant hair-treatment compositions. Non-limiting examples of amphoteric surfactants include betaines, sultaines, amphoacetates, amphoprorionates, and a mixture thereof. In some cases, one or more amphoprorionates may be used. A more exhaustive list of amphoteric surfactants that may be included in the hair-treatment compositions is provided later, under the heading "Amphoteric Surfactants."

The total amount of the one or more amphoteric surfactants may vary but is typically about 0.1 to about 25 wt. %, based on the total weight of the hair-treatment composition, including all ranges and subranges therebetween. Additionally, the total amount of the one or more amphoteric surfactants may be about 0.1 to about 20 wt. %, about 0.1 to about 15 wt. %, about 1 to about 25 wt. %, about 1 to about 20 wt. %, about 1 to about 15 wt. %, or about 5 to about 15 wt. %.

In some cases, the hair-treatment compositions may include one or more cationic polymers. Non-limiting examples of cationic polymers include poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, the one or more cationic polymers are polyquaterniums, for example, polyquaternium-11, polyquaternium-37, etc.

The total amount of the one or more cationic polymers may vary but it typically about 0.01 to about 10 wt. %, based on the total weight of the hair-treatment compositions. The total amount of the one or more cationic polymers may be about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, or about 0.1 to about 3 wt. %.

In a more specific embodiment, the hair-treatment composition is lotion comprising:
about 0.01 to about 10 wt. % of polyurethane-34;
about 0.01 to about 10 wt. %, about 0.1 to about 10 wt. %, or about 1 to about 5 wt. % of polyurethane-34;
about 0.01 to about 10 wt. %, about 0.1 to about 8 wt. %, or about 0.1 to about 5 wt. % of one or more thickening agents, for example, thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof
about 0.1 to about 20 wt. %, about 1 to about 20 wt. %, or about 1 to about 15 wt. % of one or more amphoteric surfactants, for example, amphoteric surfactants selected from the group consisting of betaines, sultaines, amphoacetates, taurates, amphoprorionates, and a mixture thereof.
about 0.1 to about 20 wt. %, about 0.1 to about 10, or about 1 to about 8 wt. % of one or more water-soluble solvents selected from the group consisting of polyhydric alcohols, glycol ethers, $C_{1-4}$ alcohols, and a mixture thereof; and
about 50 to about 90 wt. % of water.

The types of hair-treatment compositions discussed above are described in detail in U.S. Ser. No. 62/491,841, which is incorporated herein by reference in its entirety.

Hair-Treatment Composition with Polyurethane Latex Polymer and Bis-Urea Derivatives In some cases, the hair-treatment compositions include one or more polyurethane latex polymers and one or more bis-urea derivatives. For example, the hair-treatment composition may include:
one or more polyurethane latex polymers;
one or more bis-urea derivatives of the following formula:

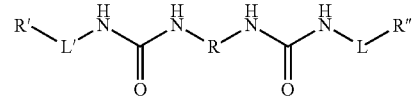

wherein R is a $C_3$-$C_{18}$ linear, branched, or cyclic moiety; and
R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;
wherein if R' and R" are the same, then both of said groups is selected from the group consisting of α-methyl branched $C_2$-$C_{18}$ ethers and β-methyl branched $C_2$-$C_{18}$ ethers;
wherein L and L' may be same or different and are selected from the group consisting of ethylene oxide chains, propylene oxide chains, and mixtures thereof, and the chains may comprise one or a plurality of repeat units; and one or more hydrophobic solvents.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

The hair-treatment compositions include one or more bis-urea derivatives, such as those set forth above. In some instances, the one or more bis-urea derivatives may be selected from the group consisting of compounds of the following formula:

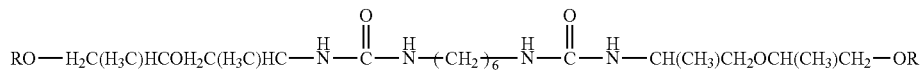

wherein R is a $C_1$-$C_{36}$ linear or branched alkane, a $C_6$-$C_{24}$ linear or branched alkane, or a $C_{10}$-$C_{16}$ linear or branched alkane. A non-limiting example of a bis-urea derivative is as follows:

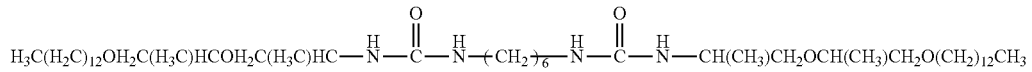

Bis-urea derivatives (such as those described above) and methods for manufacturing the bis-urea derivatives are described in U.S. Pat. No. 8,668,918, which is incorporated herein by reference in its entirety. INCI: Bis-(C12-14 alkyl PPG-4) Hexamethylenediurea is commercially available as Millithix® MT-800 (Milliken).

The total amount of the one or more bis-urea derivatives can vary but is typically about 0.1 to about 35 wt. %, based on the total weight of the hair-treatment composition. In some cases, the total amount of the one or more bis-urea derivatives is about 0.1 to about 30 wt. %, about 0.1 to about 25 wt. %, about 0.1 to about 20 wt. %, about 0.1 to about 15 wt. %, about 1 to about 35 wt. %, about to about 30 wt. %, about 1 to about 25 wt. %, about 1 to about 20 wt. %, or about 1 to about 15 wt. %.

The hydrophobic solvents suitable for use in the essentially anhydrous hair-treatment compositions are typically hydrophobic and/or non-polar. Non-limiting examples include oils, mineral oils, base oils, synthetic hydrocarbons, solid hydrocarbons, semi-solid hydrocarbons, waxes, petroleum distillates, petrolatums, and a mixture thereof. In some cases, the one or more hydrophobic solvents are oils, mineral oil, waxes, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, undecane, tridecane, 2-oleamido-1,3-octadecanediol (ceramide), and a mixture thereof. Additionally, in some cases, the one or more fatty compounds may be selected from the group consisting of brassica alcohol, cetyl esters, octyldodecanol, cetearyl alcohol, sunflower seed oil, isostearyl alcohol, and a mixture thereof.

A more exhaustive list of hydrophobic solvents that may be included in the hair-treatment compositions is provided later, under the heading "Hydrophobic Solvents."

The total amount of the one or more hydrophobic solvents can vary but is typically about 50 to about 98 wt. %, based on the total weight of the hair-treatment compositions. The total amount of the one or more hydrophobic solvents may be about 55 to about 98 wt. %, about 60 to about 98 wt. %, about 65 to about 98 wt. %, about 70 to about 98 wt. %, about 75 to about 98 wt. %, about 50 to about 97 wt. %, about 55 to about 97 wt. %, about 60 to about 97 wt. %, about 65 to about 97 wt. %, about 70 to about 97 wt. %, about 75 to about 95 wt. %, about 65 to about 80 wt. % or about 85 to about 98 wt. %.

One or more silicones may be included in the hair-treatment compositions. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. For example, in some cases, the hair-treatment compositions may include dimethicone, lauryl PEG/PPG-18/18 methicone, dimethiconol, amodimethicone, cyclomethicone, and a mixture thereof. A more exhaustive list of silicones that may be included in the hair-treatment compositions is provided later, under the heading "Silicones."

The total amount of the one or more silicones may vary but is typically about 0.01 to about 60 wt. %, based on the total weight of the hair-treatment composition. In some cases, the total amount of the one or more silicones is about 0.01 to about 50 wt. %, about 0.01 to about 40 wt. %, about 0.01 to about 30 wt. %, about 0.1 to about 60 wt. %, about 0.1 to about 50 wt. %, about 0.1 to about 40 wt. %, about 0.1 to about 30 wt. %, about 0.5 to about 50 wt. %, about 0.5 to about 40 wt. %, about 0.5 to about 30 wt. %.

One or more auxiliary agents may be included in the hair-treatment compositions. Non-limiting examples of auxiliary agents include silica, silica silicate, fumed silica, amorphous silica, clays, ceramic beads, calcium carbonate, titanium oxides, magnesium oxides, aluminium silicates and derivatives thereof, mixed silicates of natural or synthetic origin, which are optionally hydrated, natural hydrated aluminium silicates, bentonite, kaolin, Nylon, microspheres based on a copolymer of vinylidene chloride/acrylonitrile/methacrylonitrile containing isobutane, micronized or non-micronized vegetable powders, rice grain husk powders, and a mixture thereof.

The total amount of the one or more auxiliary agents may vary but is typically about 0.01 to about 10 wt. %, based on the total weight of the hair-treatment composition. The total amount of the one or more auxiliary agents may be about 0.01 to about 5 wt. %, about 0.01 to about 3 wt. %, about 0.01 to about 2 wt. %, about 0.1 to about 10 wt. %, about 0.1 to about 5 wt. %, about 0.1 to about 3 wt. %, or about 0.1 to about 2 wt. %.

In one embodiment, the hair-treatment compositions of the instant case relate to an essentially anhydrous hair-treatment composition comprising:
about 0.01 to about 10 wt. %, about 0.01 to about 5 wt. %, or about 0.1 to about 5 wt. % of polyurethane-34;
about 0.01 to about 15 wt. %, about 0.01 to about 10 wt. %, or about 0.1 to about 10 wt. % of about of BIS-(C12-14 alkyl PPG-4) hexamethylenediurea; and
about 70 to about 98 wt. % of one or more hydrophobic solvents selected from the group consisting of oils, alkanes, fatty alcohols, fatty acids, fatty alcohol derivatives, fatty acid derivatives, esters of fatty alcohols, esters of fatty acids, hydroxy-substituted fatty acids, oils, and a mixture thereof.

Furthermore, in one embodiment, the hair-treatment compositions of the instant case relate to an essentially anhydrous hair-treatment composition comprising:
about 0.01 to about 10 wt. %, about 0.01 to about 5 wt. %, or about 0.1 to about 5 wt. % of polyurethane-34;
about 0.01 to about 15 wt. %, about 0.01 to about 10 wt. %, or about 0.1 to about 10 wt. % of about of BIS-(C12-14 alkyl PPG-4) hexamethylenediurea;
about 60 to about 98 wt. %, about 65 to about 98 wt. %, or about 70 to about 98 wt. % of one or more hydrophobic solvents selected from the group consisting of oils, alkanes, fatty alcohols, fatty acids, fatty alcohol derivatives, fatty acid derivatives, esters of fatty alcohols, esters of fatty acids, hydroxy-substituted fatty acids, oils, and a mixture thereof;

about 0.01 to about 40 wt. %, about 0.1 to about 40 wt. %, or about 0.1 to about 30 wt. % of one or more silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof, in particular, cyclohexasiloxane and/or polypropylsilsequioxane.

The types of hair-treatment compositions discussed above are described in detail in U.S. Ser. No. 15/581,993, which is incorporated herein by reference in its entirety.

More exhaustive but non-limiting lists of components useful in the hair-treatment compositions disclosed herein are provided below.

Polyurethane Latex Polymers

Polyurethane latex polymers that be used in the instant hair-treatment compositions include, polyurethane latex polymers such as aqueous polyurethane dispersions comprising the reaction products of (i), (ii), and/or (iii), defined below.

Reaction product (i) may be any prepolymer according to the formula:

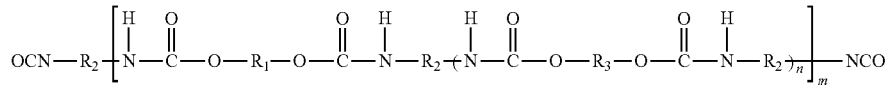

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecane¬dioic, 1,3-cyclohexanedicarboxylic, 1,4-cyclo¬hexane-dicarboxylic, 2,5-norboranedicarboxylic, diglycolic, thiodipropionic, 2,5-naphthalene-dicarboxylic, 2,6-naphthalene¬dicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythio¬ether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexane¬diol. Polyacetals useful according to various non-limiting embodiments of the disclosure can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula R2(NCO)2, in which R2 represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanato¬methyl-3,5,5-trimethylcyclohexane (isophorone diisocyanate or IPDI), bis(4-isocyanatocyclohexyl)-methane, 1,3-bis(isocyanatomethyl) cyclohexane and 1,4-bis(isocyanatomethyl)cyclohexane and bis(4-isocyanato-β-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxy¬cyclo¬hexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylol¬butanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

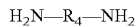

wherein $R_4$ is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophoronediamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

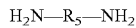

wherein $R_5$ is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, $R_5$ represents an alkylene radical substituted with sulphonic acid or sulphonate groups. By way of example only, the compound is chosen from sodium salts of N-(2-aminoethyl)-2-aminoethanesulphonic acid.

By way of non-limiting example, such polyurethane latex polymers include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989, and NEOREZ® R-2202).

Cationic Emulsifiers and/or Surfactants

Non-limiting examples of cationic emulsifiers and/or surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, stearalkonium bentonite, stearalkoniumhectonite, stearyl trihydroxyethyl propylenediamine dihydrofluoride, tallowtrimonium chloride, and hexadecyltrimethyl ammonium bromide.

The cationic emulsifiers and/or surfactants may be chosen from optionally polyoxyalkylenated, primary, secondary or tertiary fatty amines, or salts thereof, and quaternary ammonium salts, and a mixture thereof.

The fatty amines generally comprise at least one $C_8$-$C_{30}$ hydrocarbon-based chain.

Examples of quaternary ammonium salts that may especially be mentioned include: those corresponding to the general formula (III) below:

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

In some cases it is useful to use salts such as the chloride salts of the following compounds:

A. a quaternary ammonium salt of imidazoline, such as, for example, those of formula (IV) below:

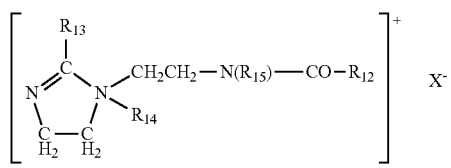

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Evonik;

B. a quaternary diammonium or triammonium salt, in particular of formula (V):

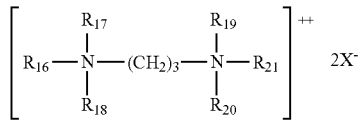

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, FINQUAT CT-P, sold by the company Innospec (Quaternium 89), and FINQUAT CT, sold by the company Innospec (Quaternium 75), C. a quaternary ammonium salt containing at least one ester function, such as those of formula (VI) below:

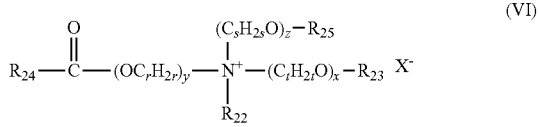

in which:
$R_{22}$ is chosen from $C_1$-$C_6$ alkyl groups and $C_1$-$C_6$ hydroxyalkyl or dihydroxyalkyl groups;
$R_{23}$ is chosen from:

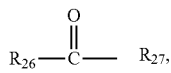

which is a linear or branched, saturated or unsaturated $C_1$-$C_{22}$ hydrocarbon-based group, and a hydrogen atom,
$R_{25}$ is chosen from:

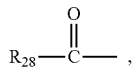

$R_{29}$, which is a linear or branched, saturated or unsaturated $C_1$-$C_6$ hydrocarbon-based group, and a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6;
y is an integer ranging from 1 to 10;
x and z, which may be identical or different, are integers ranging from 0 to 10;
$X^-$ is a simple or complex, organic or mineral anion;
with the proviso that the sum x+y+z is from 1 to 15, that when x is 0 then $R_n$ denotes $R_{27}$, and that when z is 0 then $R_{25}$ denotes $R_{29}$.

The alkyl groups $R_{22}$ may be linear or branched, and more particularly linear. In some cases, $R_{22}$ denotes a methyl, ethyl, hydroxyethyl or dihydroxypropyl group, and more particularly a methyl or ethyl group. Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms. When $R_{25}$ is an $R_{29}$ hydrocarbon-based group, it preferably contains 1 to 3 carbon atoms. Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

In some cases, x and z, which may be identical or different, have values of 0 or 1. Likewise, in some cases y is equal to 1. In some cases, r, s and t, which may be identical or different, are equal to 2 or 3, and even more particularly are equal to 2.

The anion $X^-$ is may be a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^-$ is even more particularly chloride or methyl sulfate.

Use is made more particularly, in the composition according to the invention, of the ammonium salts of formula (VI) in which:
$R_{22}$ denotes a methyl or ethyl group,
x and y are equal to 1;
z is equal to 0 or 1;
r, s and t are equal to 2;
$R_{23}$ is chosen from:

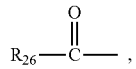

methyl, ethyl or $C_{14}$-$C_{22}$ hydrocarbon-based groups, and a hydrogen atom;
$R_{25}$ is chosen from:

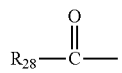

and a hydrogen atom;
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups. The hydrocarbon-based groups are advantageously linear.

Mention may be made, for example, of the compounds of formula (VI) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and a mixture thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin. Such compounds are, for example, sold under the names DEHYQUART by the company BASF, STEPANQUAT by the company Stepan, NOXAMIUM by the company Ceca or REWOQUAT WE 18 by the company Evonik.

Thickening Agents

Thickening agents (also referred to as thickeners or viscosity modifying agents) are well known. Classes of such agents include, but are not limited to, viscous liquids, such as polyethylene glycol, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition. In some cases, associative thickening polymers may be useful in anionic surfactant-free hair-treatment compositions, in particular, anionic surfactant free conditioning shampoos. For example, the anionic surfactant-free conditioning shampoos may include one or more anionic associative polymers.

Bis-Urea Derivatives

Bis-urea derivatives useful in the instant hair-treatment compositions include those of the following formula:

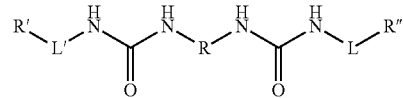

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers, wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof.

In some instances, the bis-urea derivatives may include those of the following formula:

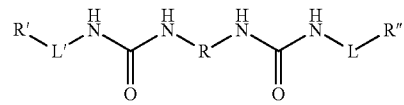

wherein R is a $C_3$-$C_{18}$ linear or branched alkylene chain or an aromatic ring; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units.

In some instances, the bis-urea derivatives may include those of the following formula:

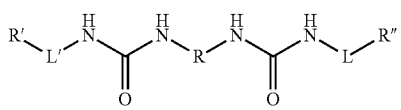

wherein R is a $C_3$-$C_{18}$ linear, branched or cyclic moiety selected from the group consisting of unsubstituted or substituted phenyl, phenyl ether, and phenyl methylene; and R' and R" may be the same or different and are selected from the group consisting of $C_1$-$C_{36}$ linear or branched alkanes, α-methyl branched $C_2$-$C_{36}$ alkanes or aryl alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units.

In particular, the bis-urea derivative may be a compound of the following formula:

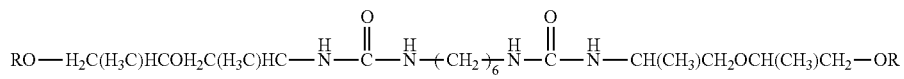

wherein R is a $C_1$-$C_{36}$ linear or branched alkane, a $C_6$-$C_{24}$ linear or branched alkane, or a $C_{10}$-$C_{16}$ linear or branched alkane. A non-limiting example of a bis-urea derivative, such as those described above is as follows:

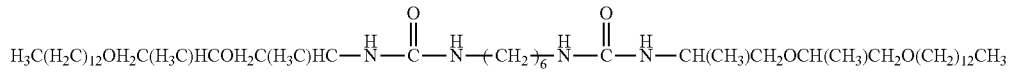

Bis-urea derivatives (such as those described above) and methods for manufacturing the bis-urea derivatives are described in U.S. Pat. No. 8,668,918, which is incorporated herein by reference in its entirety. INCI: Bis-(C12-14 alkyl PPG-4) Hexamethylenediurea is commercially available as Millithix® MT-800 (Milliken).

Fatty Compounds

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

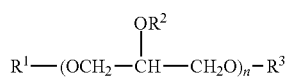

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher metling point fatty compounds may also be used, for example, fatty compounds having a metling point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Water-Soluble Solvents

The term "water-soluble solvent" is interchangeable with the term "water-miscible solvent" and means a compound that is liquid at 25° C. and at atmospheric pressure (760 mmHg), and it has a solubility of at least 50% in water under these conditions. The hair-treatment compositions of the instant disclosure may include one or more water-soluble solvents.

Water-soluble solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, proplene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

Hydrophobic Solvents

Examples of suitable hydrophobic solvents include, but are not limited to, oils, mineral white oils, solvents, base oils, technical mineral oils, synthetic hydrocarbons, solid hydrocarbons, semi-solid hydrocarbons, waxes, petroleum distillates, petrolatums, and a mixture thereof. In some instances, the solvent may be paraffinic or naphthenic oil.

Further, non-limiting examples include a diglyceride, a PPG alkyl ether, a therapeutic oil, acetylated lanolin alcohol, alexandria laurel tree oil, alkyl benzoate, alkyl octanoate, almond oil, an essential oil, an unsaturated or polyunsaturated oil, apricot stone oil, arachidyl behenate, arachidyl propionate, avocado oil, barley oil, basil oil, beeswax, benzyl laurate, benzyl myristate, benzyl palmitate, bis(octyldodecyl stearoyl) dimer dilinoleate, borage seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, cardamom oil, carrot oil, castor oil, cetearyl ethylhexanoate, cetearyl isononanoate, cetearyl octanoate, cetyl acetate, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cypress oil, decyl oleate, diethyleneglycol diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dioctyl malate, dioctyl sebacate, disopropyl adipate, dodecyl oleate, essential oils, ester derivatives of lanolic acid, ester oils, ethylhexyl cocoate, ethylhexyl ethyl hexanoate, ethylhexyl hydroxystarate, ethylhexyl isononanoate, ethylhexyl palmitate, ethylhexyl palmytate, ethylhexyl pelargonate, ethylhexyl stearate, evening primrose oil, flaxseed oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hard fat, hazelnut oil, heavy mineral oil, hempseed oil, herring oil, hexadecyl stearate, hexyl laurate, hydrocarbon oils, hydrogenated castor oil, hyssop oil, isoamyl laurate, isocetearyl octanoate, isocetyl isocetyl behenate, isocetyl lanolate, isocetyl palmitate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffin, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil, jojoba oil, lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, palm oil, passionflower oil, peanut oil, pentaerythrityl tetrastearate, petitgrain oil, petrolatum, polyisobutylene, polyolefin, poppy oil, PPG alkyl ethers, PPG-10 cetyl ether, PPG-10 oleyl ether, PPG-11 stearyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-2 butyl ether, PPG-2 methyl ether, PPG-20 butyl ether, PPG-20 oleyl ether, PPG-22 butyl ether, PPG-23 oleyl ether, PPG-24 butyl ether, PPG-26 butyl ether, PPG-28 cetyl ether, PPG-3 methyl ether, PPG-3 myristyl ether, PPG-30 butyl ether, PPG-30 cetyl ether, PPG-30 isocetyl ether, PPG-30 oleyl ether, PPG-33 butyl ether, PPG-37 oleyl ether, PPG-4 butyl ether, PPG-4 lauryl ether, PPG-4 myristyl ether, PPG-40 butyl ether, PPG-5 butyl ether, PPG-50 cetyl ether, PPG-50 oleyl ether, PPG-52 butyl ether, PPG-53 butyl ether, PPG-7 lauryl ether, PPG-9 butyl ether, PPG-9-13 butyl ether, propyl myristate, propylene glycol dicaprate, propylene glycol dicaprylate, propylene glycol myristyl ether acetate, propylene glycol ricinoleate, rapeseed oil, rosehip oil, rye oil, safflower oil, sage oil, salmon oil, sesame oil, shea butter, soya oil, soybean oil, stearyl caprate, stearyl heptanoate, stearyl propionate, sunflower oil, sweet almond oil, synthetic isoalkane, sysymbrium oil, syzigium aromaticum oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, verbena oil, walnut oil, wheat germ glycerides, wheat germ oil, white petrolatum and mixtures thereof.

Examples of suitable commercially available hydrophobic, non-polar solvents include, but are not limited to EXCEL 260-HC which is available from Excel Paralubes; ISOPAR L, ISOPAR M, and ISOPAR V which are available from Exxon Chemical; DRAKEOL 7, DRAKEOL 31, DRAKEOL 34, Snow White Petrolatum, and Amber Petrolatum which are available from Penreco; CONOSOL C145, CONOSOL 200, CONOSOL 260, and CONOSOL V 340 which are available from Conoco, Inc.; PERMETHYL 99A, PERMETHYL 101A, and PERMETHYL 102A which are available from Presperse; and PANALANE L14E which is available from Amoco.

In some instances, the hydrophobic solvent may be selected from the group consisting of oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

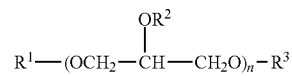

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the solvent may be one or more high melting point fatty compounds. A high melting point fatty compound is a fatty compound having a melting point of 25° C. Even higher metling point fatty compounds may also be used, for example, fatty compounds having a metling point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Silicones

Exemplary silicones include, without limitation, cyclic silicones, such as those having 3 to 6, or 3 to 4 or 3 to 5, (or any of 3, 4, 5, or 6) Si—O groups in the cyclic backbone chain (e.g., siloxanes). In some cases, the cyclic silicone is a volatile silicone. In some cases, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+d5)). Other non-limiting examples of silicones are silicones having side groups or side chains. In some cases, the side groups are hydrophobic. In some cases, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or a mixture thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si(CH$_3$)$_3$. Nonlimiting examples of silicones having branched side chains are stearyl dimethicone and phyenyltrimethicone, cetyl dimethicone, caprylyl methicone, PEG/PPG 18/18 dimethicone the structures of which are as follows:

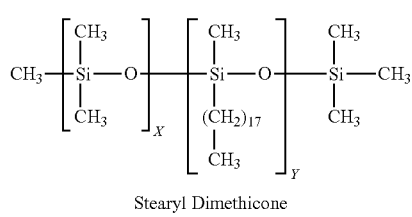

Stearyl Dimethicone

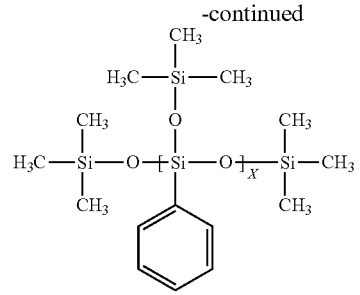

Phenyltrimethicone

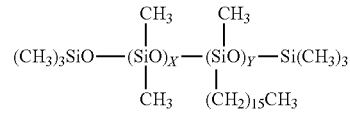

Cetyl Dimethicone

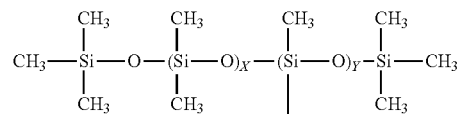

PEG/PPG 18/18 dimethicone

In the above formulas m, n, x, and y may independently be integers of 1 to 100, 1 to 80, 1 to 60, 1 to 50, 1 to 40, 1 to 30, 1 to 20, or 1 to 10. In some cases, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

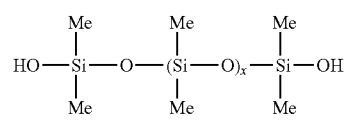

Dimethiconol

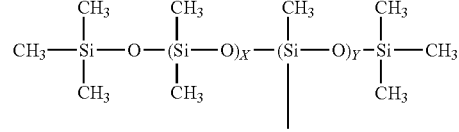

PEG/PEG 18/18 Dimethicone

X, y, m, and n are as defined above, and R is a C$_1$ to C$_{10}$ alkyl.

Another type of specific non limiting volatile silicone is a volatile short chain linear alkylmethylsilicone fluid. The volatile short chain linear alkylmethylsilicone fluid has the formula:

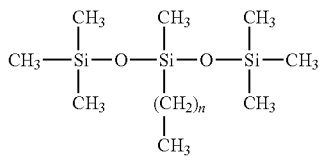

In the above formula, the integer represented by n has a value of five to twelve. Preferably, n has a value of five to eight. Compounds include, for example, 3-hexyl-1,1,1,3,5,5,5-heptamethyltrisiloxane and 3-octyl-1,1,1,3,5,5,5-heptamethyltrisiloxane.

Yet another type of volatile silicone in accordance with the present invention is a volatile short chain linear phenylmethylsilicone fluid. The volatile short chain linear phenylmethylsilicone fluid has the formula:

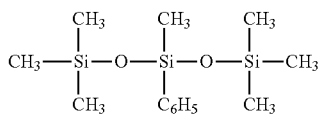

This compound is 3-phenyl-1,1,1,3,4,4,4-heptamethyltrisiloxane. Further volatile silicone fluids useful in the compositions described herein include, without limitation, are decamethylcyclopentasiloxane (DMCPS) which has a molecular weight of about 370, a refractive index of 1.40, and the formula $[(Me_2)SiO]_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45.

As amino silicone that may be used in the scope of the instant disclosure, the following can be cited:

a) polysiloxanes corresponding to formula (A):

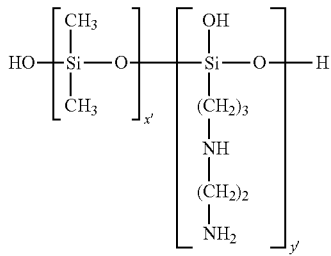

in which x' and y' are integers such that the weight-average molecular weight (Mw) is comprised between about 5000 and 500 000 b) amino silicones corresponding to formula (B):

$$R'_aG_{3-a}\text{-Si}(OSiG_2)_n\text{-}(OSiGbR'_{2-b})m\text{-}O\text{---}SiG_{3-a}\text{-}R'_a \quad (B)$$

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

R', which may be identical or different, denote a monovalent radical having formula —$C_qH_{2q}L$ in which q is a number ranging from 2 to 8 and L is an optionally quaternized amino group chosen from the following groups:

—NR"-Q-N(R")$_2$
—N(R")$_2$
—N+(R")$_3$A—
—N+H(R")$_2$A—
—N+H$_2$(R")A—
—N(R")-Q-N+R"H$_2$A—
—NR"-Q-N+(R")$_2$HA—
—NR"-Q-N+(R")$_3$A—, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

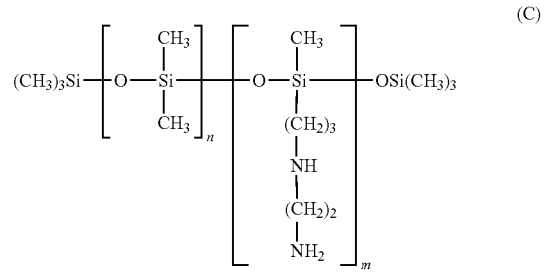

in which n and m have the meanings given above, in formula B.

Another group of amino silicones corresponding to this definition is represented by silicones having the following formulae (D) or (E):

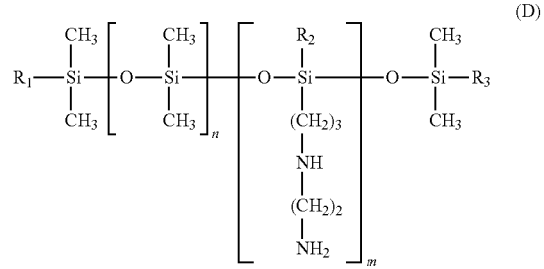

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and form to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

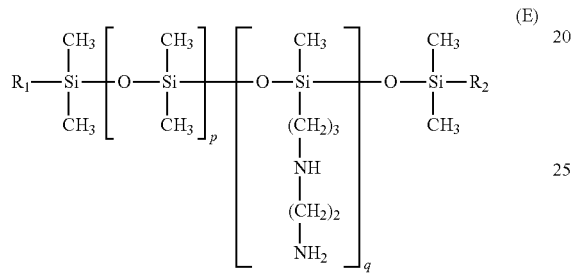

(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

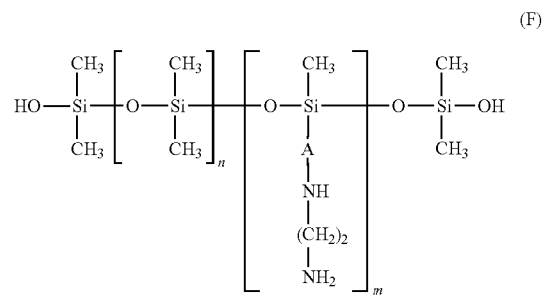

(F)

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

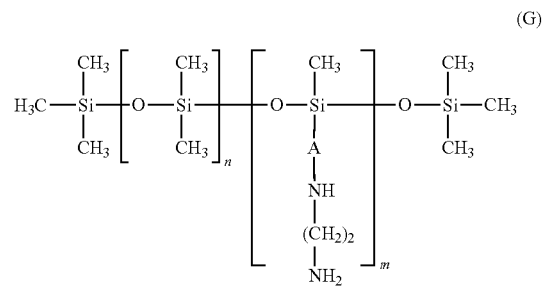

(G)

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

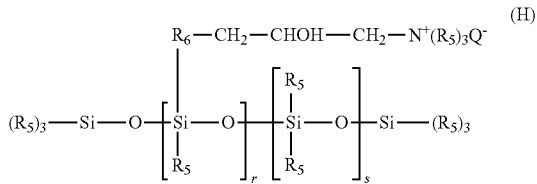

in which:
- $R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- Q- is an anion such as a halide ion, in particular chloride, or an organic acid salt (for example acetate);
- r represents a mean statistical value from 2 to 20 and in particular from 2 to 8;
- s represents a mean statistical value from 20 to 200 and in particular from 20 to 50.

Such amino silicones are described more particularly in patent U.S. Pat. No. 4,185,087.

d) quaternary ammonium silicones having formula (I):

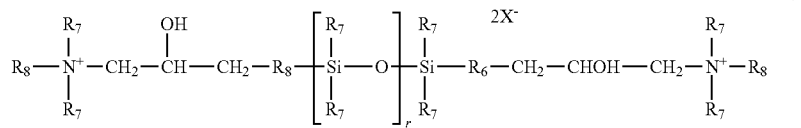

in which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCO$R_7$ radical;
- X— is an anion such as a halide ion, in particular chloride, or an organic acid salt (for example acetate);
- r represents a mean statistical value from 2 to 200 and in particular from 5 to 100;

These silicones are described, for example, in patent application EP-A 0 530 974.

e) amino silicones having formula (J):

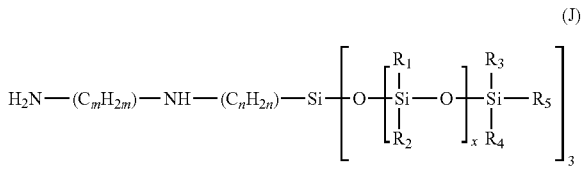

in which:
- $R_1$, $R_2$, $R_3$ and $R_4$, which may be identical or different, denote a $C_1$-$C_4$ alkyl radical or a phenyl group;
- $R_5$ denotes a $C_1$-$C_4$ alkyl radical or a hydroxyl group;
- n is an integer ranging from 1 to 5;
- m is an integer ranging from 1 to 5;

and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

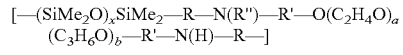

or alternatively

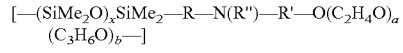

in which:
- a is an integer greater than or equal to 1, preferably ranging from 5 to 200, more particularly ranging from 10 to 100;
- b is an integer comprised between 0 and 200, preferably ranging from 4 to 100, more particularly between from 5 and 30;
- x is an integer ranging from 1 to 10 000, more particularly from 10 to 5000;
- R" is a hydrogen atom or a methyl;
- R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —CH$_2$CH$_2$CH$_2$OCH(OH)CH$_2$— radical; preferentially R denotes a —CH$_2$CH$_2$CH$_2$OCH(OH)CH$_2$— radical;
- R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —CH$_2$CH$_2$CH$_2$OCH(OH)CH$_2$— radical; preferentially R' denotes —CH(CH$_3$)—CH$_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

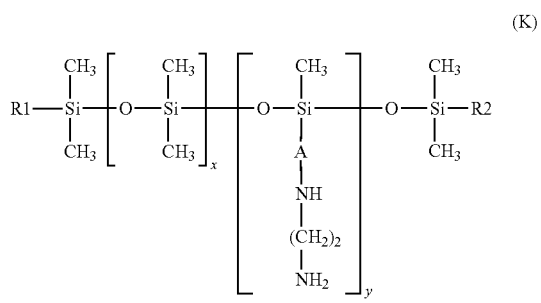

in which:
x and y are numbers ranging from 1 to 5000; preferably, x ranges from 10 to 2000 and especially from 100 to 1000; preferably, y ranges from 1 to 100;
$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;
A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$— and —$CH_2CH(CH_3)CH_2$—.

Preferably, $R_1$ and $R_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and $R_2$, which may be identical or different, are chosen from hexadecyl (cetyl) and octadecyl (stearyl) radicals.

Preferentially, the silicone is of formula (K) with:
x ranging from 10 to 2000 and especially from 100 to 1000;
y ranging from 1 to 100;
A comprising 3 to 6 carbon atoms and especially 4 carbon atoms; preferably, A is branched; and more particularly A is chosen from the following divalent radicals: $CH_2CH_2CH_2$ and —$CH_2CH(CH_3)CH_2$—; and
$R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

Preferably, the amino silicones according to the invention are chosen from the amino silicones of formula (F). A preferred silicone of formula (F) is amodimethicone (INCI name) sold under the tradename XIAMETER® MEM-8299 Cationic Emulsion by Dow Corning.

Emulsifiers

The emulsifiers are appropriately chosen according to the emulsion to be obtained (W/O or O/W). Non-limiting examples of emulsifiers may include esters of polyols and of a fatty acid having an alkyl chain containing from 12 to 22 carbon atoms, such as esters of fatty acid and of glycerol, of glucose or of sorbitol; oxyethylenated derivatives of esters of polyols and of a fatty acid having an alkyl chain containing from 12 to 22 carbon atoms, which derivatives contain from 1 to 50 oxyethylene groups, such as a complex of triisostearin (triester of glycerol and of isostearic acid) and of PEG-6; ethers of polyethylene glycol and of a fatty alcohol having an alkyl chain containing from 12 to 22 carbon atoms, which ethers contain from 1 to 50 oxyethylene groups, such as oleyl ethers and in particular oleth-25 (25 oxyethylene groups), and their mixtures.

Also included are polyol fatty esters and fatty ethers with a branched or unsaturated chain containing from 12 to 22 carbon atoms and, in particular, sorbitan monoisostearate, such as the product sold under the name "Arlacel 987" by the company ICI, sorbitan mono/dioleate, such as the product sold under the name "Arlacel 83" by the company ICI, the complex of triisostearin and of PEG-6, such as the product sold under the name "Labrafil isostearic" by the company Gattefosse, decaglyceryl pentaisostearate, such as the product sold under the name "Nikkol Decaglyn 5-IS" by the company Nikko Chemical, or methyl glucose dioleate, such as the product sold under the name "Isolan DO" by the company Goldschmidt.

Other examples of emulsifiers include esters of polyethylene glycol and of a fatty acid having an alkyl chain containing from 12 to 22 carbon atoms, which esters contain from 5 to 100 and preferably from 20 to 60 oxyethylene groups, such as PEG-40 stearate; ethers of polyethylene glycol and of a fatty alcohol having an alkyl chain containing from 12 to 22 carbon atoms, which ethers contain from 5 to 100 and preferably from 10 to oxyethylene groups, such as ceteareth-25 or ceteth-25; esters of sorbitan and of a fatty acid having an alkyl chain containing from 12 to 22 carbon atoms, which esters comprise from 0 to 100 and preferably from 4 to 25 oxyethylene groups, such as polysorbate 20, polysorbate 40 and polysorbate 60; esters of sugar and of a fatty acid having an alkyl chain containing from 12 to 22 carbon atoms, such as sucrose stearate; derivatives of polyethylene glycol and of esters of glycerol and of a fatty acid having an alkyl chain containing from 12 to 22 carbon atoms, such as PEG-8 caprylic/capric glycerides; polyethylene glycol ethers of esters of methyl glucose and of a fatty acid having an alkyl chain containing from 12 to 22 carbon atoms, such as PEG-20 methyl glucose sesquistearate; and their mixtures.

Suitable emulsifiers may be chosen from glyceryl esters and polyethylene glycol esters of stearic acid, such as glyceryl stearate and PEG-100 stearate.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name DOW CORNING 5200 Formulation Aid by the company Dow Corning; cetyldimethicone copolyol, such as the product sold under the name ABIL EM 90R by the company Evonik, and the mixture of cetyldimethicone copolyol, of polyglyceryl isostearate (4 mol) and of hexyl laurate, sold under the name ABIL WE 09 by the company Evonik. One or more co-emulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name ARLACEL P135 by the company Croda.

Glycerol and/or sorbitan esters that may be mentioned include, for example, polyglyceryl isostearate, such as the product sold under the name ISOLAN GI 34 by the company Evonik, sorbitan isostearate, such as the product sold under the name ARLACEL 987 by the company Croda, sorbitan glyceryl isostearate, such as the product sold under the name ARLACEL 986 by the company Croda, and mixtures thereof.

Emulsifying polyoxyalkylenated silicone elastomers may especially be also mentioned as those disclosed in the documents U.S. Pat. Nos. 5,236,986, 5,412,004, 5,837,793, 5,811,487, which are all incorporated herein by reference in their entirety. As examples of polyoxyethylenated silicone elastomers, mention is made of those sold by the company Shin Etsu, with the denominations: KSG-21 (at 27% in active material) INCI name: Dimethicone/PEG-10 Dimethicone vinyl dimethicone crosspolymer), KSG-20 (at 95% % in active material) INCI name: PEG-10 Dimethicone Crosspolymer), KSG-30, (at 100% % in active material) INCI name: Lauryl PEG-15 Dimethicone vinyl dimethicone crosspolymer), KSG-31 (at 25% % in active material) INCI name: Lauryl PEG-15 Dimethicone vinyl dimethicone crosspolymer), KSG-32 or KSG-42 or KSG-320 ou KSG-30 (at 25% % in active material) INCI name: Lauryl PEG-15 Dimethicone vinyl dimethicone crosspolymer), KSG-33 (at 20% in active material), KSG-210 (at 25% % in active material) INCI name: Dimethicone/PEG-10/15 crosspolymer), KSG-310: lauryl modified polydimethylsiloxane polyoxyethylenated in mineral oil, KSG-330KSG-340, X-226146 (at 32% % in active material) INCI name: Dimethicone/PEG-10 Dimethicone vinyl dimethicone crosspolymer, or those sold by the company Dow Corning under the commercial names: DC9010 (at 9% % in active material) INCI name: PEG-12 dimethicone crosspolymer) DC9011 at 11% % in active material.

Amongst water/oil emulsifiers, mention is made of polyglycerolated silicone elastomers. Non-limiting examples of polyglycerolated silicone elastomers include those sold by the company Shin Etsu, with the denominations: KSG-710, (at 25% in active material (INCI name: Dimethicone/Polyglycerin-3 Crosspolymer).

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate sold, for example, by the company Croda under the name ARLACEL 165; oxyalkylenated (oxyethylenated and/or oxypropylenated) fatty alkyl ethers; sugar esters, for instance sucrose stearate; fatty alkyl ethers of sugars, especially alkyl polyglucosides (APG) such as decylglucoside and laurylglucoside sold, for example, by the company Cognis under the respective names PLANTAREN 2000 and PLANTAREN 1200, cetostearyl glucoside optionally as a mixture with cetostearyl alcohol, sold, for example, under the name MONTANOV 68 by the company SEPPIC, under the name TEGOCARE CG90 by the company Evonik and under the name EMULGADE KE3302 by the company Cognis, and also arachidyl glucoside, for example in the form of a mixture of arachidyl alcohol, behenyl alcohol and arachidyl glucoside, sold under the name MONTANOV 202 by the company SEPPIC. According to a specific embodiment of the invention, the mixture of the alkyl polyglucoside as defined above with the corresponding fatty alcohol can be in the form of a self-emulsifying composition, for example as disclosed in the document WO-A-92/06778; the hydrophobically modified inulines as Inuline Lauryl Carbamate as the product sold under the denomination INUTEC SP1 by the Company Beneo-ORAFTI.

In some cases, the hair-treatment composition may include an emulsifier such as dimers surfactants named "gemini surfactants" and comprising two surfactant moieties identical or different, and constituted by an hydrophilic head group and a lipophilic group linked to each other through the head groups, thanks to a spacer. One can use for example a gemini surfactant such as those sold by Sasol company under the name CERALUTIOM, for example, CERALUTION H: Behenyl Alcohol, Glyceryl Stearate, Glyceryl Stearate Citrate et Sodium Dicocoyl ethylenediamine PEG-15 Sulfate, CERALUTION F: Sodium Lauroyl Lactylate et Sodium Dicocoyl ethylenediamine PEG-15 Sulfate, CERALUTION C: Aqua, Capric/Caprylic triglyceride, Glycerine, Ceteareth-25, Sodium Dicocoyl ethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben.

Among other emulsifiers, amphiphilic copolymers of 2-acrylamido 2-methylpropane sulfonic acid may be used. Non-limiting examples of AMPS copolymers include ammonium acryloyldimethyltaurate/steareth-25 methacrylate crosspolymer sold under the name ARISTOFLEX HMS by the Company Clariant, ammonium acryloyldimethyltaurate/steareth-8 methacrylate copolymer sold under the name ARISTOFLEX SNC by the company Clariant.

Amphoteric Surfactants

Amphoteric surfactants useful in the cosmetic compositions disclosed herein may be chosen from betaines, sultaines, amphoacetates, amphoproprionates, and a mixture thereof. More typically, betaines and amphoproprionates are used, and most typically betaines. Betaines which can be used in the current compositions include those having the formulas below:

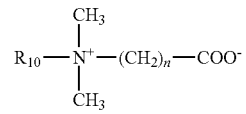

$$R_{10} - \underset{\underset{CH_3}{|}}{\overset{\overset{CH_3}{|}}{N^+}} - (CH_2)_n - COO^-$$

-continued

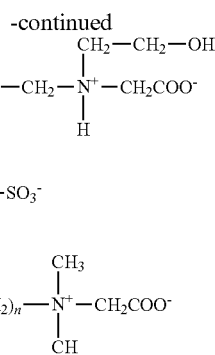

wherein $R^{10}$ is an alkyl group having 8-18 carbon atoms; and n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and a mixture thereof. Typically, the at least one betaine compound is selected from the group consisting of coco betaine, cocoamidopropyl betaine, behenyl betaine, capryl/capramidopropyl betaine, lauryl betaine, and a mixture thereof, and more typically coco betaine and/or cocoamidopropyl betaine.

Hydroxyl sultaines useful in the compositions of the invention include the following

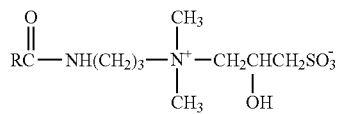

wherein

R is an alkyl group having 8-18 carbon atoms.

Useful alkylamphoacetates include those having the formula

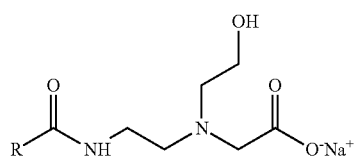

wherein

R is an alkyl group having 8-18 carbon atoms, useful alkyl amphodiacetates include those having the formula

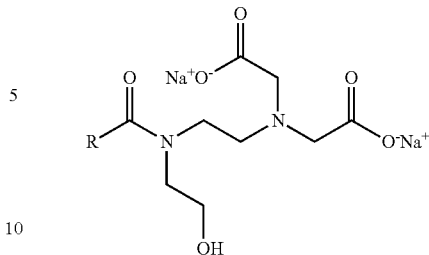

wherein

R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, ($C_8$-$C_{20}$)alkylamido ($C_1$-$C_6$)alkylbetaines, sulfobetaines, ($C_8$-$C_{20}$)alkylsulfobetaines, ($C_8$-$C_{20}$)alkylamido ($C_1$-$C_6$)alkylsulfobetaines, ($C_8$-$C_{20}$)alkylamphoacetate, ($C_5$-$C_{20}$)alkylamphodiacetate, and a mixture thereof.

Among the optionally quaternized secondary or tertiary aliphatic amine derivatives that may be used, mention may also be made of the products of respective structures (A1) and (A2) below:

$$Ra-CON(Z)CH_2-(CH_2)m-N+(Rb)(Rc) \quad (CH_2COO-) \qquad (A1)$$

in which:

Ra represents a $C_{10}$-$C_{30}$ alkyl or alkenyl group derived from an acid Ra—COOH preferably present in hydrolysed coconut oil, a heptyl group, a nonyl group or an undecyl group, Rb represents a β-hydroxyethyl group, Rc represents a carboxymethyl group;

m is equal to 0, 1 or 2,

Z represents a hydrogen atom or a hydroxyethyl or carboxymethyl group;

$$Ra'-CON(Z)CH_2-(CH_2)m'-N(B)(B') \qquad (A2)$$

in which:

B represents —$CH_2CH_2OX'$, with X' representing —$CH_2$—COOH, $CH_2$—COOZ', $CH_2CH_2$—COOH, —$CH_2CH_2$—COOZ', or a hydrogen atom, B' represents —$(CH_2)z$—Y', with z=1 or 2, and Y' representing COOH, COOZ', $CH_2$—CHOH—$SO_3H$ or —$CH_2$—CHOH—$SO_3Z'$, m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanola-mine, diethanolamine and triethanolamine, monoisopropanolamine, diisopropa-nolamine or triisopropanolamine, 2-amino-2-methyl-1-propanol, 2-amino-2-methyl-1,3-propanediol and tris(hydroxymethyl) aminomethane, Ra' represents a $C_{10}$-$C_{30}$ alkyl or alkenyl group of an acid Ra'COOH preferably pre-sent in hydrolysed linseed oil or coconut oil, an alkyl group, in particular a $C_{17}$ alkyl group, and its iso form, or an unsaturated $C_{17}$ group.

Among the compounds corresponding to formula (A2) in which X' represents an hydrogen atom, mention may be made of compounds under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroam-phodipropionate, disodium caproamphodipropionate, disodium capryloamphodi-propionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (A3):

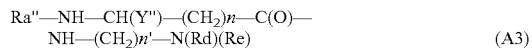

NH—$(CH_2)n'$—N(Rd)(Re)    (A3)

in which:
Ra" represents a C10-C30 alkyl or alkenyl group of an acid Ra"'—C(O)OH preferably present in hydrolysed linseed oil or coconut oil;
Y" represents the group —C(O)OH, —C(O)OZ", —$CH_2$—CH(OH)—$SO_3$H or the group $CH_2$—CH (OH)—$SO_3$—Z", with Z" representing a cationic counterion resulting from an alkali metal or alkaline-earth metal, such as sodium, an ammonium ion or an ion resulting from an organic amine;
Rd and Re represent, independently of each other, a $C_1$-$C_4$ alkyl or hydroxyalkyl radical; and
n and n' denote, independently of each other, an integer ranging from 1 to 3.

Among the compounds corresponding to formula (A3), mention may in particular be made of the compound under the name sodium diethylaminopropylcocoaspartamide.

Preferably, the amphoteric surfactants are chosen from ($C_8$-$C_{20}$)alkylbetaines, ($C_8$-$C_{20}$)alkylamido($C_1$-$C_6$)alkylbetaines, ($C_8$-$C_{20}$)alkylamphoacetates and ($C_8$-$C_{20}$)alkylamphodiacetates, and a mixture thereof.

In some cases, the at least one amphoteric surfactant is chosen from ($C_8$-$C_{20}$)alkyl betaines, ($C_8$-$C_{20}$)alkylamido ($C_1$-$C_6$)alkylbetaines, ($C_8$-$C_{20}$)alkylamphoacetate, ($C_8$-$C_{20}$) alkylamphodiacetate, and their salts, and a mixture thereof. In some cases, the at least one amphoteric surfactant is selected from coco-betaine, cocamidopropylbetaine, sodium cocoamphoacetate, disodium cocoamphodiacetate, and a mixture thereof.

Cationic Polymers

Non-limiting examples of cationic polymers include poly (methacryloyloxyethyl trimethylammonium chloride), polyquaternium-37, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic polymers are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100, and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Active Agents

Oxidizing Agents

Oxidizing agents may be selected from, for example, peroxides, persulfates, perborates percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof.

One or more oxidizing agents are typically included in an oxidizing composition. An oxidizing composition may be a hair lightening or bleaching composition or it may be a neutralizing composition or a developer composition. In some cases, the total amount of the one or more oxidizing agents in an oxidizing composition is essentially 100% (as is the case for some powdered oxidation compositions). In some cases, the total amount of the one or more oxidizing agents is about 1 to about 80 wt. %, about 1 to about 70 wt. %, about 1 to about 60 wt. %, about 1 to about 50 wt. %, about 1 to about 40 wt. %, about 5 to about 80 wt. %, about 5 to about 70 wt. %, about 5 to about 60 wt. %, about 5 to about 50 wt. %, about 5 to about 40 wt. %, about 10 to about 80 wt. %, about 10 to about 70 wt. %, about 10 to about 60 wt. %, about 10 to about 50 wt. %, or about 10 to about 40 wt. %, based on the total weight of the composition.

Reducing Agents

Reducing agents are well known for use in hair care compositions. Typical reducing agents are capable of reducing the disulfide bonds in the hair to produce free thiol groups. Non-limiting examples of suitable reducing agents include thioglycolic acid and thioglycolic acid salts and esters, thiolactic acid and thiolactic acid salts and esters, cysteine thioglycerol, thioglycolic hydrazide, thioglycolamide, glycerol monothioglycolate, sodium metabisulfite, beta-mercaptopropionic acid, N-hydroxyethyl mercapto-acetamide, N-methyl mercapto-acetamide, beta-mercapto-ethylamine, beta-mercaptopropionamide, 2-mercapto-ethanesulfonic acid, dimercaptoadipic acid, dithiothreitol, homocysteinethiolactone, cysteine derivatives, polythiol derivatives formed by the addition of cysteamine onto a maleic anhydride-alkylvinylether copolymer, inorganic sulfites, inorganic bisulfites, cysteamine and its derivatives, dithioerythritol, organic phosphines, and mixtures thereof.

One or more reducing agents may be included in reducing compositions. The total amount of the one or more reducing agents can vary, but in some cases, the total amount of the one or more reducing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Neutralizing Agents

Neutralizing agents are well known for use in hair care compositions. In some cases, after treating hair with compositions of the present disclosure comprising active agents chosen from reducing agents for curling or shaping the hair (as in perming and hair straightening systems), the hair is treated with a neutralizing agent or composition containing a neutralizing agent. For instance, the neutralizing agent may be an oxidizing agent chosen from hydrogen peroxide, urea hydrogen peroxide, alkali metal bromates, or persalts, such as perborates and persulphates. One or more neutralizing agents may be included in neutralizing compositions. The total amount of the one or more neutralizing agents can vary, but in some cases, the total amount of the one or more neutralizing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Non-Reducing Agents for Shaping Hair

Non-reducing agents for shaping hair may be one or more hydroxide compounds, non-hydroxide compounds, or mixtures thereof. For instance, the hydroxide compounds may be alkali metal hydroxides, alkaline-earth metal hydroxides, transition metal hydroxides, and mixtures thereof. Non-limiting examples include of hydroxide compounds include sodium hydroxide, potassium hydroxide, lithium hydroxide, calcium hydroxide, magnesium hydroxide, barium hydroxide, strontium hydroxide, manganese hydroxide, zinc hydroxide, guanidine hydroxide, and mixtures thereof.

Colorants

Before, after, or simultaneously with the hair lightening composition, a color-altering composition may be used. For example, the color-altering composition may be formed by combining a hair lightening composition according to the instant disclosure, a developer composition (typically comprising hydrogen peroxide) and a colorant. Typically, the coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-β-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropano-1,N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]

pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the addition salts thereof. 4,5-Diamino-1-(β-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used. 4,5-Diamino-1-(3-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-β-hydroxyethylamino-3,4-methylene-dioxybenzene, a-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylene-dioxybenzene, 2,6-bis(J-hydroxyethylamino) toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

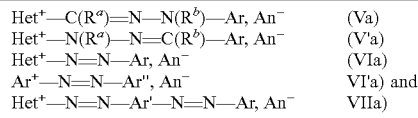

in which formulas (Va), (V'a), (VIa), (VI'a) and (VIIa):

Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N-($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar'' is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_5$)alkyl, which is optionally substituted, preferentially with a hydroxyl group;

or alternatively the substituent $R^a$ with a substituent of Het⁺ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An⁻ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

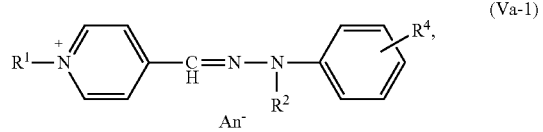

(Va-1)

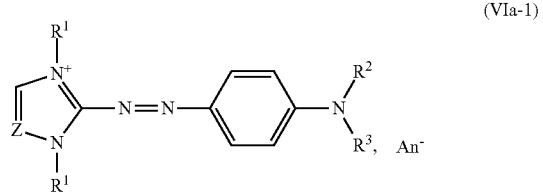

(VIa-1)

wherein in formulae (Va-1) and (VIa-1):

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

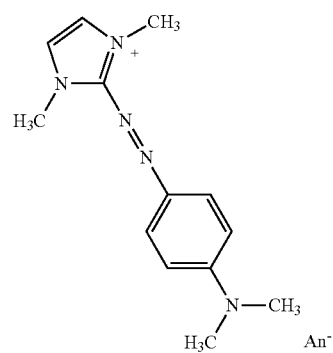

Basic Red 51

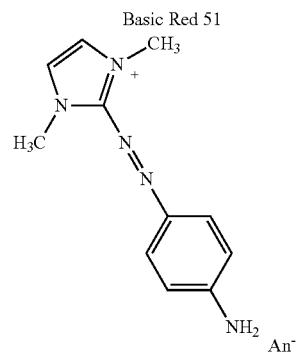

Basic Orange 31

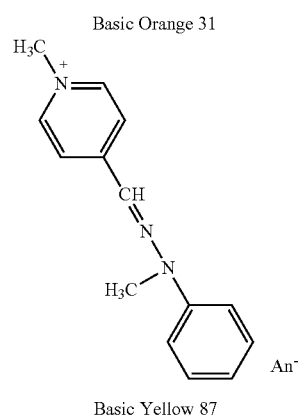

Basic Yellow 87

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Implementation of the present disclosure is provided by way of the following examples. The examples serve to illustrate the technology without being limiting in nature.

EXAMPLE 1

Polyurethane Latex Polymer and Cationic Emulsifiers

Oil-In-Water Emulsions

| Component | INCI US Name | #1 wt. % | #2 wt. % | #3 wt. % | #4 wt. % | #5 wt. % |
|---|---|---|---|---|---|---|
| Polyurethane | POLYURETHANE-34 | 0.8 | 0.8 | 0.8 | 0.8 | 0.8 |
| Cationic Emulsifier | BRASSICYL ISOLEUCINATE ESYLATE | 0.3 | 1 | 1 | 1 | 1 |
| Amino Acid | ARGININE | 0.04 | 0.04 | 0.04 | 0.04 | 0.04 |
| Fatty Compounds | *BRASSICA* ALCOHOL, CETYL ESTERS, OCTYLDODECANOL, CETEARYL ALCOHOL AND/OR SUNFLOWER SEED OIL | 7.5 | 8.1 | 8.1 | 8.1 | 8.1 |
| Emulsifiers | GLYCERYL STEARATE, BEHENETH-10 AND/OR PPG-3 BENZYL ETHER ETHYLHEXANOATE | 4.35 | 4.5 | 4.5 | 4.5 | 4.5 |
| Water-Soluble Solvent | GLYCERIN | 2 | 2 | 2 | 2 | 2 |
| Cationic Polymers | POLYQUATERNIUM-11 AND/OR POLYQUATERNIUM-72 | — | — | 1 | 1 | 1 |
| Fragrance(s) | OPTIONAL COMPONENT | 0-2 | 0-2 | 0-2 | 0-2 | 0-2 |
| Thickener(s) | OPTIONAL COMPONENT | 0-2 | 0-2 | 0-2 | 0-2 | 0-2 |
| Preservative(s) | OPTIONAL COMPONENT | 0-2 | 0-2 | 0-2 | 0-2 | 0-2 |
| Water | Water | Q.S. | Q.S. | Q.S. | Q.S. | Q.S. |

EXAMPLE 2

Polyurethane Latex Polymer and Cationic Emulsifier

Oil-In-Water Emulsions

| Component | INCI US Name | #6 wt. % | #7 wt. % | #8 wt. % |
|---|---|---|---|---|
| Polyurethane | POLYURETHANE-34 | 1 | 1 | 1 |
| Cationic Emulsifier/Surfactant | BEHENTRIMONIUM CHLORIDE | 1.2 | 1 | 1.2 |
| Silicone | LAURYL PEG/PPG-18/18 METHICONE AND/OR DIMETHICONE | 0.2 | 0.4 | 2.4 |
| Film-Forming Polymer | POLYVINYLPYRROLIDONE/VINYL ACETATE (VP/VA) COPOLYMER | | 0.5 | |
| Water-Soluble Solvents | GLYCERIN AND/OR ISOPROPYL ALCOHOL | 1.3 | 1.2 | 1.3 |
| Fatty Compounds | CETYL ESTERS, ISOSTEARYL ALCOHOL, AND/OR CETEARYL ALCOHOL | 3 | 2.8 | 3.1 |

-continued

| Component | INCI US Name | #6 wt. % | #7 wt. % | #8 wt. % |
|---|---|---|---|---|
| Thickener(s) | OPTIONAL COMPONENT | 0-3 | 0-3 | 0-3 |
| Preservative(s) | OPTIONAL COMPONENT | 0-3 | 0-3 | 0-3 |
| Water | WATER | Q.S. | Q.S. | Q.S. |

EXAMPLE 3

Polyurethane Latex Polymer and Thickening Agents

Gels

| Component | INCI US | #9 wt. % | #10 wt. % | #11 wt. % | #12 wt. % | #13 wt. % |
|---|---|---|---|---|---|---|
| Polyurethane | POLYURETHANE-34 | 1 | 1 | 2 | 1 | 1 |
| Thickening Agents | HYDROXYETHYLCELLULOSE, POLYACRYLAMIDE, HYDROXYPROPYL GUAR, CARBOMER, POTATO STARCH MODIFIED, AND/OR STARCH ACETATE | 0.6 | 0.6 | 1.1 | 2 | 1 |
| Film-Forming Polymers | PVP, ACRYLATES COPOLYMER, AND/OR VP/DIMETHYLAMINO-ETHYLMETHACRYLATE COPOLYMER | 1 | | | 4.9 | 0.6 |
| Cationic Polymer | POLYQUATERNIUM-4 AND/OR POLYQUATERNIUM-11 | | 0.2 | 0.3 | | 0.2 |
| Silicone | PHENYL TRIMETHICONE, DIMETHICONE, PEG/PPG-17/18 DIMETHICONE, DIMETHICONOL, PEG-40/PPG-8 METHYLAMINOPROPYL/HYDROXYPROPYL DIMETHICONE COPOLYMER, SILICONE QUATERNIUM-16/GLYCIDOXY DIMETHICONE CROSSPOLYMER, AMINOPROPYL PHENYL TRIMETHICONE, AND/OR CROTONIC ACID/VINYL C8-12 ISOALKYL ESTERS/VA/BIS-VINYLDIMETHICONE CROSSPOLYMER | 19 | 19.4 | 7.8 | | 19 |
| Water-Soluble Solvents | GLYCERIN, DIPROPYLENE GLYCOL, PENTYLENE GLYCOL, HEXYLENE GLYCOL, PROPYLENE GLYCOL, AND/OR CAPRYLYL GLYCOL | 48 | 48.4 | 2.8 | 3.2 | 0.1 |
| Humectants (Sugar Alcohols) | HYDROGENATED STARCH HYDROLYSATE | | | | 1.1 | |
| Fatty Compound | C13-16 ISOPARAFFIN AND/OR PEG-40 HYDROGENATED CASTOR OIL | 1.3 | 1.3 | | 0.7 | 0.3 |
| Cationic Surfactants | BEHENTRIMONIUM CHLORIDE AND CETEARYL ALCOHOL (AND) BEHENTRIMONIUM METHOSULFATE | | | 0.4 | | |
| pH Adjuster | OPTIONAL COMPONENT | 0-3 | 0-3 | 0-3 | 0-3 | 0-3 |
| Preservative(s) | OPTIONAL COMPONENT | 0-3 | 0-3 | 0-3 | 0-3 | 0-3 |
| Fragrance(s) | OPTIONAL COMPONENT | 0-3 | 0-3 | 0-3 | 0-3 | 0-3 |
| Water | WATER | Q.S. | Q.S. | Q.S. | Q.S. | Q.S. |

EXAMPLE 4

Polyurethane Latex Polymer and Thickening Agent

Water-In-Oil Emulsions

| Component | INCI US | #14 wt. % | #15 wt. % | #16 wt. % |
|---|---|---|---|---|
| Polyurethane | POLYURETHANE-34 | 0.8 | 0.8 | 2.5 |
| Thickening Agent | POLYACRYLAMIDE | 0.8 | 0.8 | 2.5 |
| Film-Forming Polymer | VP/DIMETHYLAMINOETHYLMETHACRYLATE COPOLYMER | | | 9 |
| Emulsifiers | OCTYLDODECYL XYLOSIDE, PEG-30 DIPOLYHYDROXYSTEARATE AND/OR LAURETH-7 | 0.9 | 0.9 | 0.8 |
| Fatty Compound | C13-14 ISOPARAFFIN, ISONONYL ISONONANOATE, HYDROGENATED POLYISOBUTENE, AND/OR OCTYLDODECANOL | 10.6 | 10.6 | 8.2 |
| Water-Soluble Solvent | ROPYLENE GLYCOL | | | 1.5 |
| Humectants (Sugar Alcohols) | HYDROGENATED STARCH HYDROLYSATE, XYLITYL GLUCOSIDE, XYLITOL AND/OR ANHYDROXYLITOL | | 3 | 1.5 |
| pH Adjuster(s) | OPTIONAL COMPONENT | 0-3 | 0-3 | 0-3 |
| Fragrance(s) | OPTIONAL COMPONENT | 0-3 | 0-3 | 0-3 |
| Preservative(s) | OPTIONAL COMPONENT | 0-3 | 0-3 | 0-3 |
| Water | WATER | Q.S. | Q.S. | Q.S. |

EXAMPLE 5

Polyurethane Latex Polymer and Thickening Agent

Oil-In-Water Emulsion

| Component | INCI US | #17 wt. % |
|---|---|---|
| Polyurethane | POLYURETHANE-34 | 1 |
| Thickening Agents | HYDROXYPROPYL GUAR AND/OR POTATO STARCH MODIFIED | 0.7 |
| Film-Forming Polymer | PVP | 2.9 |
| Fatty Compounds | BEESWAX, SHEA BUTTER, CETEARYL ALCOHOL AND/OR CETYL ESTERS | 14.3 |
| Emulsifiers | GLYCERYL STEARATE AND/OR CETEARYL GLUCOSIDE | 4.4 |
| Cationic Polymer | POLYQUATERNIUM-11 | 0.2 |
| Silicone | PHENYL TRIMETHICONE | 0.3 |
| Water-Soluble Solvent | GLYCERIN | 2 |
| Fragrance(s) | OPTIONAL COMPONENT | 0-3 |
| Preservative(s) | OPTIONAL COMPONENT | 0-3 |
| Water | WATER | Q.S |

EXAMPLE 6

Polyurethane Latex Polymer and Thickening Agent

Lotions

| Component | INCI US | #18 wt. % | #19 wt. % |
|---|---|---|---|
| Polyurethane | POLYURETHANE-34 | 0.8 | 0.8 |
| Thickening Agents | POLYACRYLAMIDE, POTATO STARCH MODIFIED, AND/OR PEG-120 METHYL GLUCOSE TRIOLEATE | 3.2 | 4.0 |
| Amphoteric Surfactant | SODIUM COCOAMPHOPROPIONATE | 12 | 12 |
| Emulsifier | LAURETH-7 | 0.3 | 0.3 |
| Cationic Polymer | POLYQUATERNIUM-11 | | 0.2 |
| Water-Soluble Solvent | PROPYLENE GLYCOL | 1.6 | 1.6 |
| Fatty Compound | C13-14 ISOPARAFFIN | 0.8 | 0.8 |
| Fragrance(s) | OPTIONAL COMPONENT | 0-3 | 0-3 |
| Preservative(s) | OPTIONAL COMPONENT | 0-3 | 0-3 |
| Water | WATER | Q.S. | Q.S. |

EXAMPLE 7

Polyurethane Latex Polymer and Bis-Urea Derivative

Essentially Anhydrous Compositions

| Component | INCI US | #20 wt. % | #21 wt. % |
|---|---|---|---|
| Polyurethane | POLYURETHANE-34 | 0.2 | 0.2 |
| Bis-Urea Derivative | BIS-(C12-14 ALKYL PPG-4) HEXAMETHYLENEDIUREA | 8 | 2 |
| Solvent | C12-15 ALKYL BENZOATE | 91.3 | 97.3 |
| Water* | WATER | 0.5 | 0.5 |

*Note that polyurethane-34 is supplied in water.

The bis-(C12-14 alkyl PPG-4) hexamethylenediurea has a gelling temperature of about 60° C. Therefore, all raw materials are added at a temperature of about 70° C. or higher so that at 65-70° C., homogenization can be stopped to allow for uniform gelling.

EXAMPLE 8

Polyurethane Latex Polymer and Bis-Urea Derivative

Essentially Anhydrous Compositions

| Component | INCI US | #22 wt. % | #23 wt. % |
|---|---|---|---|
| Polyurethane | POLYURETHANE-34 | 1 | 0.2 |
| Bis-Urea Derivative | BIS-(C12-14 ALKYL PPG-4) HEXAMETHYLENEDIUREA | 8 | 0.5 |
| Silicone | POLYPROPYLSILSEQUIOXANE AND/OR CYCLOHEXASILOXANE | 0.9 | 25.7 |
| Solvent | C12-15 ALKYL BENZOATE, ISOPROPYL MYRISTATE, ISODODECANE, ISONONYL ISONONANOATE, AND/OR ETHYLHEXYL PALMITATE | 87.7 | 72.8 |
| Auxiliary Agent | SILICA SILICATE | 0.3 | 0.3 |
| Water* | WATER | 2.1 | 0.4 |

*Note that polyurethane-34 is supplied in water.

Isopropyl myristate and bis-(C12-14 Alkyl PPG-4) hexamethylenediurea were combined, heated to 75-80° C., and homogenized until uniform. Separately, the silica silicate and the C12-15 alkyl benzoate were combined and then the polyurethane-34 and the polypropylsilsequioxane (and) isododecane were added. This combination was then added to the mixture of the Isopropyl myristate and bis-(C12-14 Alkyl PPG-4) and homogenized at 75-80° C. before cooling to room temperature.

EXAMPLE 9

Attributes

Chemical Relaxer Composition

| | INCI US Name | wt. % |
|---|---|---|
| Active | SODIUM HYDROXIDE (100%) | 2.1 |
| Fatty Compounds | PETROLEUM JELLY, COCOA BUTTER, MINERAL OIL, AND/OR SHEA BUTTER | 36 |
| Surfactants | PEG-75 LANOLIN, CETEARYL ALCOHOL, BEHENTRIMONIUM METHOSULFATE, AND/OR POLYSORBATE 60 | 12.8 |
| Cationic Polymer | POLYQUATERNIUM-6 | 0.5 |
| Solvent | PROPYLENE GLYCOL | 3 |
| Fragrance | OPTIONAL COMPONENT | 0-2 |
| Water | WATER | Q.S |

Neutralizing Shampoo

| | INCI US Name | wt. % |
|---|---|---|
| Surfactant | SODIUM LAURETH SULFATE, COCAMIDOPROPYL BETAINE, HYDROXYPROPYLTRIMONIUM HONEY, PPG-5-CETETH-10 PHOSPHATE, POLYSORBATE 20, AND/OR POLYSORBATE 21 | 22 |
| Cationic Polymer | POLYQUATERNIUM-7 | 0.8 |
| Water-Soluble Solvent | HEXYLENE GLYCOL | 0.4 |
| pH Modifier | SODIUM HYDROXIDE | 0.3 |
| Salt | SODIUM CHLORIDE | 0.4 |
| Fragrance | OPTIONAL COMPONENT | 0-3 |
| Preservative | OPTIONAL COMPONENT | 0-3 |
| Water | WATER | Q.S |

Conditioner

| | INCI US Name | wt. % |
|---|---|---|
| Active Conditioning Agent | CITRIC ACID PROPYLENE GLYCOL DICAPRYLATE/DICAPRATE | 0.5 1 |
| Surfactant | HYDROXYPROPYLTRIMONIUM HONEY, GLYCERYL STEARATE, PEG-100 STEARATE, PPG-1 TRIDECETH-6, DICETYLDIMONIUM CHLORIDE, AND/OR STEARAMIDOPROPYL DIMETHYLAMINE | 4.7 |
| Solvent | PROPYLENE GLYCOL | 0.4 |
| Fatty Compound | MINERAL OIL AND/OR SHEA BUTTER | 3.1 |
| Cationic Polymer | POLYQUATERNIUM-37 | 1.5 |
| Vitamin | PANTHENOL | 0.1 |
| Chelating Agent | PENTASODIUM PENTETATE | 0.04 |
| Fragrance | FRAGRANCE | 0.4 |
| Preservative | PHENOXYETHANOL | 0.7 |
| Water | WATER | Q.S. |

Testing was carried out to determine the influence of hair-treatments compositions comprising a polyurethane latex polymer on chemically relaxed hair. Hair swatches were treated according to one of the following protocols:

(1) The hair swatches were treated with the chemical relaxer composition described above for about 20 minutes. The hair was shampooed, conditioned, blow dried, and evaluated.
(2) The hair swatches were treated with the chemical relaxer composition described above followed by treatment with the hair-treatment composition of Formulation #13 in Example 3 mixed with a shampoo. Formulation #13 in Example 3 was mixed in the hands with the neutralizing shampoo disclosed above (about a 1:1 ratio) and applied to the hair. After rinsing the shampoo/hair treatment composition mixture from the hair, the hair was conditioned, blow dried, and evaluated.
(3) The hair swatches were treated with the chemical relaxer composition described above. The hair was then shampooed, followed by treatment with the hair-treatment composition of Formulation #13 in Example 3 mixed with a conditioner. Formulation #13 in Example 3 was mixed in the hands with the conditioner disclosed above (about a 1:1 ratio) and applied to the hair. After rinsing the conditioner/hair-treatment composition from the hair, the hair was blow dried and evaluated.
(4) The hair swatches were treated with the chemical relaxer composition described above followed by treatment with the hair-treatment composition of Formulation #13 in Example 3 mixed with both a shampoo and subsequently with the hair-treatment composition of Formulation #13 in Example 3 mixed with a conditioner. Formulation #13 in Example 3 was mixed in the hands with the shampoo disclosed above (about a 1:1 ratio) and applied to the hair. After rinsing the shampoo/hair-treatment composition mixture from the hair, Formulation #13 in Example 3 was mixed in the hands with the conditioner disclosed above (about a 1:1 ratio) and applied to the hair. After rinsing the conditioner/hair-treatment composition mixture from the hair, the hair was blow dried and evaluated.

The components of the chemical relaxer composition, the shampoo, and the conditioner used in the testing are provided in the tables above. The hair-swatches treated according to the above protocols were evaluated by a panel of experts to determine the degree of discipline, frizz-reduction, style-control, shine, smoothness, softness/suppleness, and long-lastingness (after 1 week of treatment). The results are presented in the following table, where "✓" represents the baseline for each attribute for the hair swatches treated with only the chemical relaxer composition. "✓✓" represents an appreciable improvement in the attribute; and "✓✓✓" represents a significant improvement in the attribute.

| Attribute | Relaxer Alone | Relaxer + #13 Mixed in Shampoo | Relaxer + #13 Mixed in Conditioner | Relaxer + #13 Mixed in Shampoo and Mixed in Conditioner |
|---|---|---|---|---|
| Discipline | ✓ | ✓✓ | ✓✓ | ✓✓✓ |
| Frizz-Reduction | ✓ | ✓✓ | ✓✓ | ✓✓ |
| Style-Control | ✓ | ✓✓ | ✓✓ | ✓✓✓ |
| Shine | ✓ | ✓ | ✓ | ✓ |
| Smoothness | ✓ | ✓✓ | ✓✓ | ✓✓✓ |
| Softness/suppleness | ✓ | ✓✓ | ✓✓ | ✓✓✓ |
| Long-lastingness (after 1 week) | ✓ | ✓✓✓ | ✓✓✓ | ✓✓✓ |

The results show that all attributes except shine appreciably improved regardless of whether the hair-treatment composition was mixed with the shampoo, the conditioner, or both the shampoo and the conditioner. When the hair-treatment composition of Formulation #13 in Example 3 was mixed with both the shampoo and the conditioner and applied to the hair, a significant improvement was observed with respect to discipline, style-control, smoothness, softness/suppleness, and long-lastingness (after 1 week).

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

Some of the various categories of components identified for the hair-treatment compositions may overlap. For example, overlap may exist between some thickening agents and some cationic polymers. In such cases where overlap may exist and the hair-treatment composition includes both components (or the hair-treatment composition includes more than two components that overlap), an overlapping compound does not represent more than one component. For example, a homopolymer of methyl quaternized dimethylaminoethyl methacrylate crosslinked by a crosslinking agent may be considered both a cationic polymer and a thickening agent. If a particular hair-treatment composition includes both a cationic polymer component and a thickening agent component, a single homopolymer of methyl quaternized dimethylaminoethyl methacrylate crosslinked by a crosslinking agent will serve as only the cationic polymer or only the thickening agent (the compound does not serve as both the cationic polymer and the thickening agent).

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat," and its grammatical variations, relates to contacting hair with the hair-treatment compositions of the present disclosure.

The term "rinse," in the context of the instant disclosure, is used as customarily understood in the hair-care/hair-treatment art. For example, when a hair-treatment composition (e.g., a shampoo, conditioner, etc.) is "rinsed" from the hair, it is understood that at least some or most of the hair-treatment composition is removed from the hair. Nonetheless, in many cases, at least a residual amount of the hair-care composition or ingredient(s) from the hair care composition remains in or on the hair. In fact, in some cases, the residual amount of remaining composition or ingredient(s) is at least in part responsible for one or more of the styling benefits imparted to the hair.

A "rinse-off" hair-treatment composition refers to a composition that is rinsed and/or washed with water either after or during the application of the composition onto the hair, and before drying and/or styling the hair. At least a portion, and typically most, of the composition is removed from the hair during the rinsing and/or washing.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

The term "essentially anhydrous" or "substantially anhydrous" as used herein, for example, in the context of an "essentially anhydrous hair-treatment composition" or a "substantially anhydrous hair-treatment composition" means that the composition includes less than about 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for treating chemically treated hair comprising:
    applying a hair-treatment composition to chemically treated hair within 30 minutes from when a chemical treatment composition is rinsed from the hair, the hair-treatment composition comprising:
        one or more polyurethane latex polymers;
        one or more silicone-organic polymer hybrid compounds;
        one or more additional silicones that are different than the one or more silicone-organic polymer hybrid compounds; and
        water; and
    rinsing the hair-treatment composition from the hair within 30 minutes from applying the hair-treatment composition to the hair.

2. A method of claim 1, wherein the hair-treatment composition is applied to wet or damp hair.

3. A method of claim 1, wherein the one or more polyurethane latex polymers are selected from the group consisting of polyurethane-32, polyurethane-34, polyurethane-35, polyurethane-48, and a mixture thereof.

4. A method of claim 1, further comprising:
    styling the hair within 30 minutes from rinsing the hair-treatment composition from the hair.

5. A method of claim 4, wherein styling the hair comprises drying the hair with a blow drier or shaping the hair with a hot iron.

6. A method of claim 1, wherein the hair-treatment composition is combined with a shampoo and/or a conditioner, or a conditioning shampoo prior to application to the chemically treated hair.

7. A method of claim 6, wherein the hair-treatment composition is combined with both a shampoo and a conditioner; and the shampoo is applied first to the hair and then rinsed from the hair, and the conditioner is applied second to the hair and then rinsed from the hair.

8. A method of claim 7, wherein the hair-treatment composition is combined with a shampoo, a conditioner, or a conditioning shampoo in a ratio of about 1:5 to about 5:1 (hair treatment composition : shampoo, conditioner, or conditioning shampoo).

9. A method of claim 1 comprising:
applying a hair-treatment composition to the hair;
applying a shampoo, a conditioner, or a conditioning shampoo to the hair before rinsing the hair-treatment composition from the hair; and
rinsing the hair-treatment composition and the shampoo, conditioner, or conditioning shampoo from the hair together.

10. A method of claim 1 comprising:
applying a shampoo, conditioner, or conditioning shampoo to the hair before applying a hair-treatment composition to the hair;
without rinsing the shampoo, conditioner, or conditioning shampoo from the hair, applying the hair-treatment composition to the hair; and
rinsing the hair-treatment composition and the shampoo, conditioner, or conditioning shampoo from the hair together.

11. A method of claim 1 further comprising:
applying a chemical treatment composition to hair and chemically treating the hair prior to applying the hair-treatment composition to the chemically treated hair.

12. A method of claim 1 comprising
applying a chemical treatment composition to hair and chemically treating the hair;
rinsing the chemical treatment composition from the hair;
combining a hair-treatment composition with a shampoo and applying the hair-treatment composition and shampoo to the hair within 30 minutes from rinsing the chemical treatment composition from the hair;
rinsing the hair-treatment composition and shampoo from the hair together within 30 minutes of applying the hair-treatment composition and shampoo to the hair;
combining a hair-treatment composition with a conditioner and applying the hair-treatment composition and conditioner to the hair within 30 minutes of rinsing the hair-treatment composition and shampoo from the hair;
rinsing the hair-treatment composition and conditioner from the hair within 30 minutes of applying the hair-treatment composition and the conditioner to the hair; and
styling the hair.

13. A method of claim 1, wherein the one or more additional silicones that are different than the one or more silicone-organic polymer hybrid compounds are selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof.

14. A method of claim 1, wherein the hair-treatment composition further comprises:
one or more thickening agents.

15. A method of claim 1, wherein the hair-treatment composition further comprises:
one or more cationic polymers.

16. A method of claim 1, wherein the hair-treatment composition is in the form of an emulsion comprising:
about 0.01 to about 10 wt. % of polyurethane-34;
about 0.01 to about 10 wt. % of crotonic acid/vinyl C8-12 isoalkyl esters/VA/bis-vinyldimethicone crosspolymer;
about 1 to about 50 wt. % of one or more silicones selected from the group consisting of dimethicone, dimethiconol, phenyl trimethicone, cyclomethicone, amodimethicone, trimethyl silyl amodimethicone, trimethyl siloxy silicate, and mixtures thereof;
about 0.01 to about 10 wt. % of one or more thickening agents selected from the group consisting of hydroxypropyl guar gum, hydroxyethyl cellulose, starch-based polymers, and a mixture thereof;
about 0.01 to about 10 wt. % of one or more cationic polymers comprising a polquaternium; and
about 50 to about 95 wt. % of water.

17. A method of claim 1, wherein the hair-treatment composition comprises:
one or more polyurethane latex polymers;
one or more thickening agents;
one or more water soluble solvents; and
water.

18. A method of claim 17, wherein the hair-treatment composition is in the form of a gel comprising:
about 0.01 to about 10 wt. % of polyurethane-34;
about 0.01 to about 10 wt. % of one or more thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
about 20 to about 60 wt. % of one or more water-soluble solvents selected from the group consisting of polyhydric alcohols, glycol ethers, $C_{1-4}$ alcohols, and a mixture thereof;
about 0.01 to about 15 wt. % of one or more silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof; and
about 15 to about 90 wt. % of water.

19. A method of claim 1, wherein the hair-treatment composition comprises:
one or more polyurethane latex polymers;
one or more thickening agents;
one or more emulsifiers;
one or more fatty compounds; and
water.

20. A method of claim 19, wherein the hair-treatment composition is in the form of an emulsion comprising:
about 0.01 to about 10 wt. % of polyurethane-34;
about 0.01 to about 10 wt. % of one or more thickening agents selected from the group consisting of selected from the group consisting of polyacrylamide, cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
about 0.1 to about 15 wt. % of one or more emulsifiers selected from the group consisting of alkylpolyglycosides, glyceryl esters, ethylene glycol esters, propylene glycol esters and sucrose esters of fatty acids, ethoxylated fatty alcohols, ethoxylated fatty acids, partial glycerides of ethoxylated fatty acids, polyglycerolated fatty acid triglycerides, and a mixture thereof;
about 1 to about 40 wt. % of one or more fatty compounds selected from the group consisting of C13-14 isoparaffin, isononyl isonanoate, hydrogenated polyisobutene, shea butter, cetearyl alcohol, and cetyl esters, isononanoate, and a mixture thereof; and
water.

21. A method of claim 1, wherein the hair-treatment composition comprises:
one or more polyurethane latex polymers;
one or more thickening agents;
one or more amphoteric surfactants; and
water.

22. A method of claim 21, wherein the hair-treatment composition is in the form of a lotion comprising:
about 0.01 to about 10 wt. % of polyurethane-34;
about 0.01 to about 10 wt. % of one or more thickening agents selected from the group consisting of selected from the group consisting of cross linked acrylic acid polymers (carbomer), methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, guar gum, hydroxypropyl guar gum, starch, modified starch, starch-based polymers, methylhydroxypropyl starch, and a mixture thereof;
about 1 to about 20 wt. % of one or more amphopropionate surfactants;
about 0.1 to about 20 wt. % of one or more water-soluble solvents selected from the group consisting of polyhydric alcohols, glycol ethers, $C_{1-4}$ alcohols, and a mixture thereof; and
about 50 to about 90 wt. % of water.

23. A method of claim 1, wherein the hair-treatment composition is an essentially anhydrous composition comprising:
one or more polyurethane latex polymers;
one or more bis-urea derivatives of formula (I):

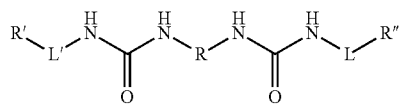

wherein R is a $C_3$-$C_{18}$ linear, branched, or cyclic moiety; and

R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, (β-methyl branched $C_2$-$C_{36}$ alkanes, and β-methyl branched $C_2$-$C_{36}$ ethers;
wherein if R' and R" are the same, then both of said groups is selected from the group consisting of α-methyl branched $C_2$-$C_{18}$ ethers and (β-methyl branched $C_2$-$C_{18}$ ethers;
wherein L and L' may be same or different and are selected from the group consisting of ethylene oxide chains, propylene oxide chains, and mixtures thereof, and the chains may comprise one or a plurality of repeat units; and
one or more hydrophobic solvents.

24. A method of claim 23, wherein the hair-treatment composition further comprises:
one or more silicones.

25. A method of claim 23, wherein the hair-treatment composition further comprises:
one or more auxiliary agents.

26. A method of claim 23, wherein the hair-treatment composition is an essentially anhydrous composition comprising:
about 0.01 to about 10 wt. % of polyurethane-34;
about 0.1 to about 10 wt. % of BIS-(C12-14 alkyl PPG-4) hexamethylenediurea; and
about 70 to about 98 wt. % of one or more solvents selected from the group consisting of oils, alkanes, fatty alcohols, fatty acids, fatty alcohol derivatives, fatty acid derivatives, esters of fatty alcohols, hydroxyl-substituted fatty acids, waxes, and a mixture thereof.

27. A method of claim 23, wherein the hair-treatment composition is an essentially anhydrous composition comprising:
about 0.01 to about 10 wt. % of polyurethane-34;
about 0.1 to about 10 wt. % of BIS-(C12-14 alkyl PPG-4) hexamethylenediurea;
about 60 to about 98 wt. % of one or more solvents selected from the group consisting of oils, alkanes, fatty alcohols, fatty acids, fatty alcohol derivatives, fatty acid derivatives, esters of fatty alcohols, hydroxyl-substituted fatty acids, waxes, and a mixture thereof
about 0.01 to about 40 wt. % of one or more silicones selected from the group consisting of ; and
about 0.01 to about 10 wt. % of one or more auxiliary agents.

* * * * *